United States Patent [19]

Kozarich et al.

[11] Patent Number: 5,686,416
[45] Date of Patent: *Nov. 11, 1997

[54] INCREASING BLOOD-BRAIN BARRIER PERMEABILITY WITH PERMEABILIZER PEPTIDES

[75] Inventors: John W. Kozarich, Cambridge; Gary F. Musso, Hopkington; Bernard Malfroy-Camine, Arlington, all of Mass.

[73] Assignee: Alkermes, Inc., Cambridge, Mass.

[*] Notice: The term of this patent shall not extend beyond the expiration date of Pat. No. 5,268,164.

[21] Appl. No.: 133,169
[22] PCT Filed: Apr. 23, 1992
[86] PCT No.: PCT/US92/03352
§ 371 Date: Nov. 12, 1993
§ 102(e) Date: Nov. 12, 1993
[87] PCT Pub. No.: WO92/18529
PCT Pub. Date: Oct. 29, 1992

Related U.S. Application Data

[63] Continuation-in-part of Ser. No. 690,522, Apr. 23, 1991, Pat. No. 5,268,164.
[51] Int. Cl.⁶ .......... A61K 38/02; A61K 38/08; C07K 7/18
[52] U.S. Cl. .......... 514/15; 530/314; 530/323; 930/30; 930/DIG. 600
[58] Field of Search .......... 514/15; 530/314, 530/328, 323; 930/30, 31, DIG. 600, DIG. 601, DIG. 602

[56] References Cited

U.S. PATENT DOCUMENTS

| | | | |
|---|---|---|---|
| 3,364,193 | 1/1968 | Hempel et al. | 530/314 |
| 4,923,963 | 5/1990 | Stewart et al. | 530/314 |
| 5,112,596 | 5/1992 | Malfroy-Camine | 424/2 |
| 5,154,924 | 10/1992 | Friden | 530/311 |
| 5,162,497 | 11/1992 | Coy et al. | 530/314 |
| 5,268,164 | 12/1993 | Kozarich | 424/9 |

FOREIGN PATENT DOCUMENTS

| | | | |
|---|---|---|---|
| 1 803 492 | 6/1969 | Germany. | |
| WO 89/09231 | 10/1989 | WIPO. | |
| 9116355 | 10/1991 | WIPO | C07K 99/18 |

OTHER PUBLICATIONS

European J. Pharmacology, vol. 155, issued 1988, Drapeau et al, "[Phe⁸ ψ(CH₂–NH)Arg⁹]bradykinin . . . ", pp. 193–195.

Br. J. Pharmacology, vol. 99, issued 1990, Rhaleb et al, "Structure–activity studies on bradykinin . . . ", pp. 445–448.

Kyle, et al., "Design and Conformational Analysis of Several Highly Potent Bradykinin Receptor Antagonists," *J. Med. Chem.*, 34(3): 1230–1233 (1991).

Wahl, M., et al., "Effects of Bradykinin on Pial Arteries and Arterioles In Vitro and In Situ," *J. Cere. Blood Flow and Metab.*, 3: 231–237 (1983).

Unterberg, A. and Baethmann, A.J., "The Kallikrein–Kinin System as Mediator in Vasogenic Brain Edema," *J. Neurosurg.*, 61: 87–96 (1984).

(List continued on next page.)

*Primary Examiner*—Jeffrey E. Russel
*Attorney, Agent, or Firm*—Hamilton, Brook, Smith & Reynolds, P.C.

[57] ABSTRACT

Peptides called receptor mediated permeabilizers (RMP) increase the permeability of the blood-brain barrier to molecules such as therapeutic agents or diagnostic agents. The permeabilizer A-7 or conformational analogues can be intravenously co-administered to a host together with molecules whose desired destination is the interstitial fluid compartment of the brain. Alternatively, the permeabilizer A-7 or conformational analogues can be administered sequentially with the molecule(s) of interest and these molecules can also be administered by routes other than intravascular. The permeabilizer A-7 or conformational analogues allow these molecules to penetrate the blood-brain barrier and arrive in the interstitial fluid.

8 Claims, 19 Drawing Sheets

OTHER PUBLICATIONS

Unterberg, A., et al., "Effects of Bradykinin on Permeability and Diameter of Pial Vessels In Vivo," *J. Cere. Blood Flow and Metab.*, 4: 574–585 (1984).

Wahl, et al., "Cerebrovascular Effects of Bradykinin," *Neural Regulation of Brain Circulation*, C. Owman and J.E. Hardebo, eds., Elsevier Science Publ., pp. 419–430 (1986).

Olesen, S.-P. and Crone, C., "Substances that Rapidly Augment Ionic Conductance of Endothelium in Cerebral Venules," *Acta Physiol. Scand.*, 127: 233–241 (1986).

Wahl. M., et al., "Effects of Bradykinin on Credbral Haemodynamics and Blood–Brain Barrier Function," In: Peptidergic Mechanisms in Cerebral Circulation (Edwinssen and McCulloch, Eds) Chichester, Herwood: 166–190 (1987).

Wahl, M., et al., "Mediators of Blood–Brain Barrier Dysfunction and Formation of Vasogenic Brain Edema," *J. Cere. Blood Flow and Metab.*, 8: 621–634 (1988).

Raymond, J.J., et al., "Pharmacological Modufication of Bradykinin Induced Breakdown of the Blood–Brain Barrier," *Can. J. Neuro. Sci.*, 13: 214–220 (1986).

Saria, A., et al., "Vascular Protein Leakage in Various Tissues Induced by Substance P, Capsaicin, Bradykinin, Serotonin, Histamine and by Antigen Challenge," *Naunyn–Schniedeberg's Arch. Pharmacol.*, 324: 212–218 (1983).

Kamitani, T., et al., "Evidence for a Possible Role of the Brain Kallikrein–Kinin System in the Modulation of the Cerebral Circulation," *Circulation Research*, 57(4): 545–552 (1985).

Schurer, L., et al., "Blood–Brain Barrier Permeability and Vascular Reactivity to Bradykinin after Pretreatment with Dexamethasone," *Acta Neuropathol.*, 77: 576–581 (1989).

Marceau, et al., "Pharmacology of Kinins: Their Relevance to Tissue Injury and Inflammation," *Gen. Pharmac.*, 14(2), 209–229 (1983).

Hiesiger, et al., "Opening the Blood–Brain and Blood–Tumor Barriers in Experimental Rat Brain Tumors: The Effect of Intracarotid Hyperosmolar Mannitol on Capillary Permeability and Blood Flow," *Annals Neurology*, 19(1): 50–59 (1986).

Barry, et al., "Amphotericin B and the Blood–Brain Barrier to Methotrexate," *Neurosurgery*, 10(2): 224–226 (1982).

Williams, et al., "Pharmacokinetics of Interferon in Blood, Cerebrospinal Fluid, and Brain after Administration of Modified Polyriboinosinic–Polyribocytidylic Acid and Amphotericin B," *J. Inf. Diseases*, 146(6): 819–825 (1982).

Ayre, "New Approaches to the Delivery of Drugs to the Brain," *Medical Hypotheses*, 29: 283–291 (1989).

Unterberg, A., et al., "Blood Flow, Metabolism, and Function of the Brain During Cerebral Administration of Bradykinin," *Advances in Neurosurgery*, 13: 326–329 (1985).

Chemical Abstracts, vol. 105, No. 19, 10 Nov. 1986, Columbus, OH, U.S.; Abstract No. 164987q.

Rhaleb, et al., "Structure–Activity Studies on Bradykinin and Related Peptides: Agonists," *Br. J. Pharmacol.* 99, 445–448 (1990).

INCREASING BLOOD-BRAIN BARRIER PERMEABILITY WITH PERMEABILIZER PEPTIDES

This application is the U.S. National Phase of PCT/US92/03352 filed Apr. 23, 1992 which is a Continuation-in-Part of U.S. application Ser. No. 07/690,522, filed Apr. 23, 1991 (now U.S. Pat. No. 268,164), the teachings of which are incorporated herein by reference.

BACKGROUND

As our understanding of the nervous system and its related disorders increases, a wider range of therapeutic and diagnostic agents will become available. Once these agents have been identified, it will be necessary to deliver them to sites of diseased tissue in the central nervous system. Unfortunately, the existence of the blood-brain barrier limits the free passage of many types of molecules from the blood to cells of the central nervous system.

The physiological basis for the blood-brain barrier is the brain capillaries, which are comprised of endothelial cells (Goldstein, et al., *Scientific American*, 255:74–83 (1986); Pardridge, W. M., *Endocrin. Rev.*, 7:314–330 (1986)). These endothelial cells are different from those found in other tissues of the body. In particular, they form complex tight junctions between themselves. The actual blood-brain barrier is formed by these high-resistance tight intercellular junctions which, with the cells themselves, form a continuous wall against the passive movement of many molecules from the blood to the brain. These cells are also different in that they have few pinocytotic vesicles, which in other tissues allow somewhat unselective transport across the capillary wall. In addition, continuous gaps or channels running through the cells, which would allow unrestrained passage, are absent.

One function of the blood-brain barrier is to protect the brain from fluctuations in blood chemistry. However, this isolation of the brain from the bloodstream is not complete. There does exist an exchange of nutrients and waste products. The presence of specific transport systems within the capillary endothelial cells assures that the brain receives, in a controlled manner, all of the compounds required for normal growth and function. The obstacle presented by the blood-brain barrier is that, in the process of protecting the brain, it excludes many potentially useful therapeutic and diagnostic agents.

Several techniques exist that either physically break through the blood-brain barrier or circumvent it to deliver therapeutic or diagnostic agents. Among these are intrathecal injections, surgical implants, and osmotic techniques.

Intrathecal injection allows administration of agents directly into the brain ventricles and spinal fluid by puncturing the membranes surrounding the brain. Sustained delivery of agents directly into the spinal fluid can be attained by the use of infusion pumps that are implanted surgically. These spinal fluid delivery techniques are used to treat brain cancers, infections, inflammation and pain. However, they do not penetrate deeply into the brain.

Clinicians prefer to avoid intrathecal injections because they frequently are ineffective and can be dangerous. Substances injected intrathecally are distributed unevenly, slowly and incompletely in the brain. Since the volume of the spinal fluid is small, increases in intracerebral pressure can occur with repeated injections. Furthermore, improper needle or catheter placement can result in seizure, bleeding, encephalitis and a variety of other severe side effects.

An osmotic approach has been used by Dr. Edward Neuwelt at the University of Oregon to deliver chemotherapeutics and imaging antibodies to tumors in the brain. (Neuwelt, E. A., Implication of the Blood-Brain Barrier and its Manipulation, Vols 1 & 2, Plenum Press, N.Y. (1989)). This technique involves an arterial injection of a bolus of a hypertonic mannitol solution. The osmotic differential exerted by the mannitol causes the endothelial cells forming the barrier to shrink, opening gaps between them for a brief period. During this period, the drug is administered into the arterial system and is carried directly into the brain. The osmotic approach demonstrates that once past the barrier, therapeutic agents can be effectively distributed throughout the brain.

Because of the many risks involved, a 24- to 48-hour period in an intensive care unit is necessary following osmotic treatment. Mannitol can cause permanent damage (including blindness) to the eye. If the barrier is permeable for too long, brain edema results. Cells of the brain also can be damaged when neurotoxic substances in the blood, not generally accessible to the brain, are able to cross the barrier. Finally, there is a serious incidence of seizures in patients during and after the procedure.

SUMMARY OF THE INVENTION

The present invention pertains to compositions for increasing the permeability of the blood-brain barrier in an animal. These compositions are permeabilizers of the blood-brain barrier which are peptides having a core sequence of amino acids or amino acid analogues. In the core peptide, the sequence is arginine-proline-hydroxyproline-glycine-thienylalanine-serine-proline-4-Me-tyrosine-$\psi(CH_2NH)$ arginine (SEQ ID No.:1), from N-terminal to C-terminal, where $\psi(CH_2NH)$ denotes a reduced peptide bond between the 4-Me-tyrosine and arginine amino acids. This peptide, which is an analogue of bradykinin, is referred to herein, for convenience, as permeabilizer A-7. Conformational analogues of this sequence are also compositions of this invention provided they have the property of increasing the permeability of the blood-brain barrier.

Pharmaceutical compositions that include permeabilizer A-7 or conformational analogues and a pharmaceutically acceptable carrier are also encompassed in this invention. These pharmaceutical compositions can also include one or more molecules for which the permeabilizer A-7 or conformational analogues make the blood-brain barrier more permeable.

Finally, the present invention pertains to a method for increasing the permeability of the blood-brain barrier of a host to a molecule contained in the host's bloodstream. This method comprises the administration of an effective amount of permeabilizer A-7 or conformational analogues to the host. The molecule, for which the blood-brain barrier is made more permeable by the administered permeabilizer A-7 or conformational analogues, can also be co-administered with the permeabilizer A-7 or conformational analogues in this invention. Thus, the molecule to be delivered across the blood-brain barrier to the brain can be either an endogenous molecule residing in the bloodstream or an exogenous molecule that is co-administered sequentially or simultaneously with permeabilizer A-7 or conformational analogues.

An advantage of the present invention is that it provides a practical means for increasing the permeability of the blood-brain barrier by the administration of permeabilizer A-7 or conformational analogues while co-administering a molecule of therapeutic, prophylactic or diagnostic value. For example, intravenous injection of permeabilizer A-7 or conformational analogues is significantly less invasive than intrathecal injection or osmotic disruption of the blood-brain barrier. The permeabilizer A-7 or conformational analogues preferentially increase the permeability of the blood-brain barrier for lower molecular weight substances.

The permeabilizer A-7 or conformational analogues of this invention can be administered by one of the traditional routes of administration. That is, the permeabilizer A-7 or conformational analogues can be administered by such techniques as intravascular, subcutaneous or intramuscular injections, oral, transdermal or intranasal administrations, and inhalation or sustained release routes. These routes of administration provide a variety of available options for delivering the permeabilizer A-7 or conformational analogues of this invention into the bloodstream of the host.

DETAILED DESCRIPTION OF THE INVENTION

Figure 1:
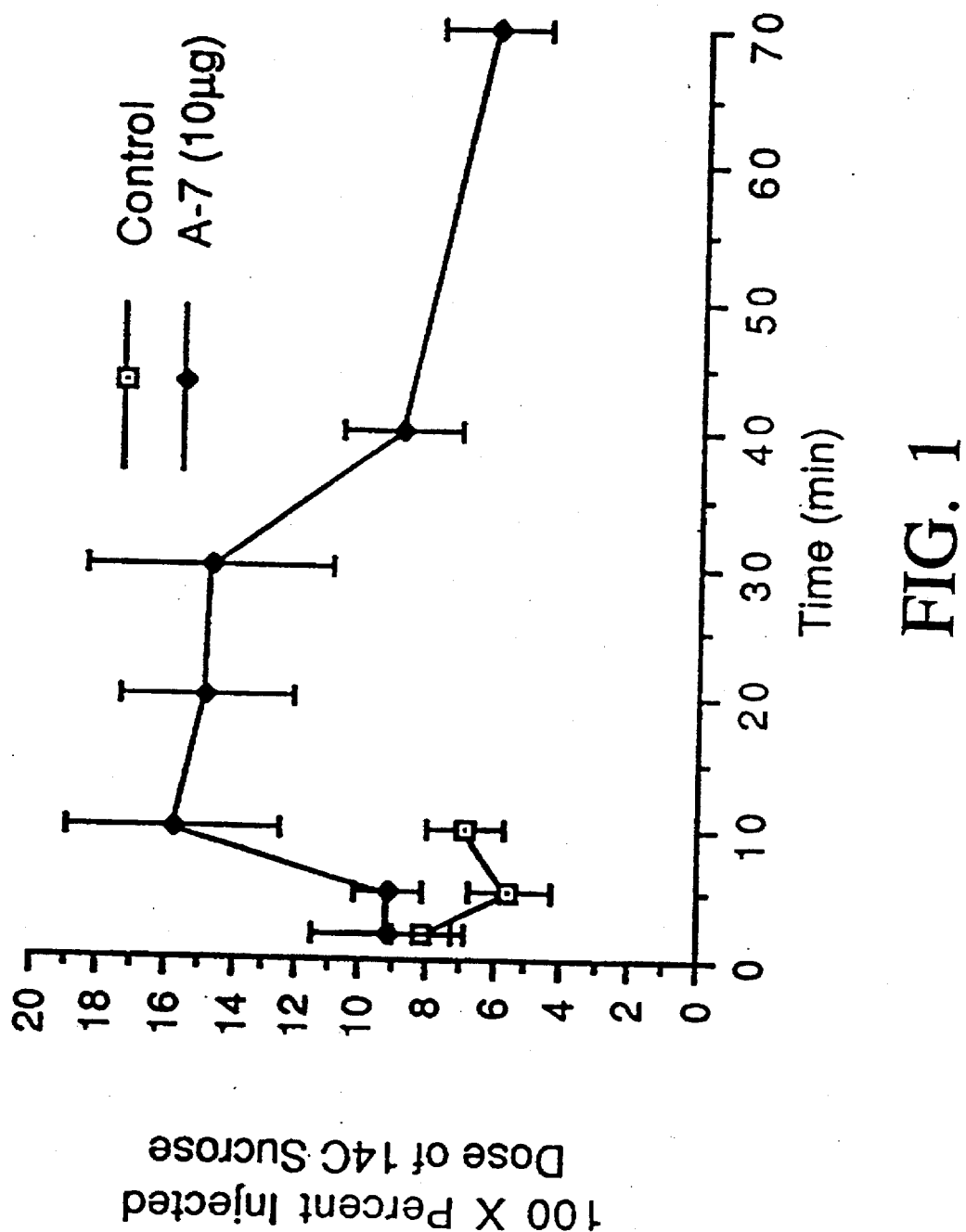
FIG. 1 is a graphic representation of the time course of brain uptake of sucrose after the administration of a specific amount (10 µg) of permeabilizer A-7 into different mice.

This invention pertains to compositions for increasing the permeability of the blood-brain barrier in an individual, such as a human being, to a molecule of interest. By increasing the permeability of the blood-brain barrier to the molecule of interest, the molecule more readily leaves the bloodstream and enters the interstitial fluid of the brain. The increase in blood-brain barrier permeability to the molecule of interest provides accessibility of this molecule to the brain in higher relative concentrations than without the permeabilizer A-7 or conformational analogues.

The compositions of the invention are referred to as permeabilizer A-7 or conformational analogues. This term has been chosen to characterize the attribute of these substances for increasing the permeability of the blood-brain barrier to a molecule of interest. The increased permeability of the blood-brain barrier that occurs as a result of the administration of these compositions is believed to be mediated by receptors, probably bradykinin $B_2$ receptors, located on the surface of brain endothelial cells that form the blood-brain barrier. The interaction between these receptors and the compositions of the invention apparently alters junctional or transport properties between the cells thereby increasing the permeability of the blood-brain barrier to molecules such as the molecule of interest. These molecules more freely penetrate the blood-brain barrier as a result of this interaction of permeabilizer A-7 or conformational analogues at the receptors.

The substance known as bradykinin can also increase the permeability of the blood-brain barrier to molecules. This permeability increase probably occurs by the same mechanism as that for the permeabilizer A-7 or conformational analogues of this invention. That is, bradykinin probably interacts at the same or similar $B_2$ receptors as the permeabilizer A-7 or conformational analogues to cause an alteration of the blood-brain barrier permeability so that certain molecules can more easily leave the bloodstream to enter the interstitial fluid of the brain. For this reason, the permeabilizer A-7 or conformational analogues of this invention and bradykinin may be considered to be pharmacological agonists for increasing permeability of the blood-brain barrier.

The permeabilizer A-7 or conformational analogues of this invention, like bradykinin, are peptides or peptidomimetics having a core sequence of amino acids. This core sequence of amino acids has such a conformation in aqueous solution that it can interact with molecules associated with the blood-brain barrier, e.g. receptor molecules, to effect an increase in the permeability of the blood-brain barrier to a molecule of interest that resides in or is injected into the bloodstream. The specific sequence of amino acids or mimetic replacements of the various permeabilizer A-7 or conformational analogues confers the proper conformation to them so they interact with the molecules associated with the blood-brain barrier to cause an increase in the permeability of the blood-brain barrier. If the primary sequence is improper, the substance will not adopt the proper conformation and thus will not effect an increase in the permeability of the blood-brain barrier.

The proper conformation that allows the permeabilizer A-7 or conformational analogues to interact with molecules to effect an increase in the permeability of the blood-brain barrier puts a restriction on the structure of the amino acids that compose the permeabilizer A-7 or conformational analogue sequence of this invention. Only particular sequences of amino acids and mimetics of these amino acids will fulfill the criterion for being a member of the family of permeabilizer A-7 or its conformational analogues; namely, that they allow the proper conformation so they can effect an increase in the permeability of the blood-brain barrier.

A specific and preferred embodiment of this invention is the permeabilizer A-7 with the linear amino acid sequence from N-terminal to C-terminal of: arginine-proline-hydroxyproline-glycine-thienylalanine-serine-proline-4-Me-tyrosineψ(CH$_2$NH)-arginine (SEQ. ID NO.:1). This peptide is referred to herein as permeabilizer A-7. A method for synthesis of permeabilizer A-7 is given in the Examples. However, other known preparative methods can be employed to produce permeabilizer A-7 or conformational analogues.

This peptide, permeabilizer A-7, differs from a conventional peptide sequence of amino acids in the following ways: the third amino acid is hydroxyproline; the fifth amino acid is thienylalanine which is similar to phenylalanine but where a thienyl group has replaced the phenyl group; the eighth amino acid is tyrosine which has been substituted with a methyl group at the 4 position; and the peptide bond between the eighth and ninth amino acids has been replaced with a reduced peptide bond isostere, i.e. ψ(CH$_2$NH). Peptide and peptidomimetic analogues of this embodiment are also part of this invention provided they allow the proper conformation in aqueous solution so they effect an increase in permeability of the blood-brain barrier to molecules of interest. These compositions are termed "conformational analogues" of this embodiment.

This permeabilizer A-7 or conformational analogues may be compared to bradykinin which has the following linear amino acid sequence: arginine-proline-proline-glycine-phenylalanine-serine-proline-phenylalanine-arginine (SEQ. ID NO.:2) (Lehninger, A. L., *Biochemistry*, p. 75 (1975)). The preferred permeabilizer A-7 differs from bradykinin in the following respects: at the third amino acid, hydroxyproline replaces proline; at the fifth amino acid, thienylalanine replaces phenylalanine; at the eighth amino acid, 4-Me-tyrosine replaces phenylalanine; and between the eighth and ninth amino acids, a reduced peptide bond replaces a conventional peptide bond. These differences make the preferred permeabilizer A-7 more effective for increasing the permeability of the blood-brain barrier when compared to bradykinin. Much less of the permeabilizer A-7 is required to increase the blood-brain barrier permeability and more of the molecule of interest crosses the blood-brain barrier at a given administered amount of the permeabilizer A-7 when compared to the same administered amount of bradykinin.

Characteristic features of the permeabilizer A-7 or conformational analogues of this invention are important for the permeabilizer A-7 or conformational analogues to allow the proper conformation to effect an increase in the permeability of the blood-brain barrier to one or more molecules of interest. For example, the following modifications can be made to permeabilizer A-7, yet allow the proper conformation to be formed: the N-terminal arginine is replaced by an amino acid analogue containing a guanidino or guanidino derivative side chain; the second amino acid (proline) is replaced by hydroxyproline, dehydroproline, N-methylalanine or another proline analogue; the third amino acid (hydroxyproline) is replaced by proline, dehydroproline, another proline analogue, alanine, sarcosine or N-methylalanine; the fifth amino acid (thienylalanine) is replaced by another aromatic amino acid or a hydrophobic aliphatic amino acid; the sixth amino acid (serine) is replaced by glycine, threonine, alanine, allothreonine, asparagine, glutamine or analogues thereof; the seventh amino acid (proline) is replaced by hydroxyproline, dehydroproline, N-methylalanine or another proline analogue; the eighth amino acid (4-Me-tyrosine) is replaced by another O-alkyl tyrosine or a hydrophobic aliphatic amino acid; the C-terminal arginine is replaced by an amino acid analogue containing a guanidino side chain; and the peptidomimetic isosteric bond between the eighth amino acid (4-Me-tyrosine) and the C-terminal amino acid (arginine), ψ(CH$_2$NH), is replaced by ψ(CSNH), ψ(NHCO) or ψ(CH$_2$S).

Within this general scheme for obtaining conformational analogues of permeabilizer A-7, it is preferred that the changes be limited to: β-cycloarginine, homoarginine, γ-hydroxyarginine, canavanine, N$^\omega$-amidinocitrulline, 2-amino-4-guanidinobutanoic acid, citrulline, homocitrulline or cyanoguanidino derivatives of either lysine or ornithine for the N-terminal or C-terminal arginine; hydroxyproline or dehydroproline for the second or seventh amino acids (proline); proline or dehydroproline for the third amino acid (hydroxyproline); dehydrophenylalanine, phenylalanine or another aromatic analogue or leucine, isoleucine, valine, cyclohexylalanine or another aliphatic amino acid for the fifth amino acid (thienylalanine); glycine or threonine for the sixth amino acid (serine); and O-alkyl tyrosine or leucine, isoleucine, valine, cyclohexylalanine or another aliphatic amino acid for the eighth amino acid (4-Me-tyrosine).

With these specified amino acid designations, the proper conformation of the permeabilizer A-7 or conformational analogues is achieved so that the permeabilizer A-7 or conformational analogues can effect an increase in the permeability of the blood-brain barrier to a molecule of interest. These amino acid positions and designations appear to be important for the permeabilizer A-7 or conformational analogues to allow the proper conformation so that the desired interaction can occur.

Another variation that is within this invention is the optional addition of one or more amino acids or analogues to the N-terminal arginine or the masking of the primary amino group of this arginine (e.g. acetylation). These additional amino acids are linked by typical peptide bonds to each other and to the N-terminal arginine, thus making the additional amino acid(s) the N-terminal region of the permeabilizer A-7 or conformational analogue peptide. These additional amino acids are arginine or lysine or, if there are two additional amino acids, the N-terminal amino acid can be methionine. If a single amino acid is added and is arginine, it can be substituted with an acetyl or other masking agent (e.g. propyl, benzyl, adamantylacetyl, etc.) These additional amino acids can be of the D- or the L-isomeric form. Preferred additional N-terminal amino acid groups are arginine-, acetyl arginine-, lysine-, arginine—arginine-, lysine—lysine-, methionine-arginine- or methionine-lysine- where these additional amino acids are of either D or L configuration.

The amino acids that constitute the core sequence of the permeabilizer A-7 or conformational analogues of this invention preferably should be formed as the L-isomer. The D-isomer can be substituted at some positions of the core sequence (e.g. position 8) and the resulting peptide will still have blood-brain barrier permeabilizing activity. However, if the D-isomer is substituted at position 9 of the core constituent amino acids of the sequence, the increase in permeability of the blood-brain barrier is severely attenuated when the resulting permeabilizer A-7 or conformational analogue is administered to the host animal.

This invention also pertains to pharmaceutical compositions suitable for administration to host animals to increase the permeability of the blood-brain barrier to a molecule of interest. These pharmaceutical compositions contain one or more of the permeabilizer A-7 or conformational analogues in a pharmaceutically acceptable carrier known to one of skill in the art. The pharmaceutical composition will often be given by injection into a blood vessel of the host animal. In particular, the pharmaceutical composition can be administered intravenously since the permeabilizer A-7 or conformational analogues are not significantly degraded by angiotensin converting enzyme (ACE) known to be present in high concentrations in the lung. By contrast, bradykinin is significantly degraded by ACE and therefore is often administered intra-arterially.

The quantity of permeabilizer A-7 or conformational analogues to be administered, and therefore packaged as units of the pharmaceutical composition, depends upon the efficacy of permeabilizer A-7 or the chosen conformational analogue, the size and other individual variations of the host compared to the population of hosts as a whole and the molecule(s) of interest to be passed through the blood-brain barrier. The actual amounts and concentrations of permeabilizer A-7 or conformational analogues in the pharmaceutical compositions can be readily ascertained by a person of skill in the art.

The pharmaceutical compositions of this invention can also contain one or more molecules of interest to be passed across the blood-brain barrier. In these compositions, both the molecule(s) of interest and the permeabilizer A-7 or conformational analogue that foster(s) its (their) penetration of the blood-brain barrier can be included in a convenient package. This allows the substances to be co-administered so the efficiency of administration of these substances is maximized.

In some instances, such packaging will not be advantageous. Many times, the molecule(s) of interest and the permeabilizer A-7 or conformational analogue will be administered sequentially in order to allow one of the moieties to be at optimal concentration in the blood before the other moiety is administered. In these situations, the moieties will be separately packaged.

This invention also relates to a method for increasing the permeability of the blood-brain barrier of a host to a molecule present in the host's bloodstream. The host can be any animal which possesses a central nervous system (i.e., a brain). Examples of hosts include mammals, such as humans, domestic animals (e.g, dog, cat, cow or horse) and animals intended for experimental purposes (e.g., mice, rats, rabbits).

The amount of permeabilizer A-7 or conformational analogue administered to a host that is efficacious for increasing the permeability of the blood-brain barrier is below the toxic level for that host. Thus, nontoxic dosages of permeabilizer A-7 or conformational analogues can be administered without sacrificing permeabilizing activity.

The molecule in the host's bloodstream can be exogenous to the host. For example, it can be a neuropharmaceutical agent which has a therapeutic or prophylactic effect on a neurological disorder. Examples of neurological disorders include cancer (e.g., brain tumors), Acquired Immune Deficiency Syndrome (AIDS), infections of the central nervous system, epilepsy, Parkinson's disease, multiple sclerosis, neurodegenerative disease, trauma, depression, Alzheimer's disease, migraine, pain, or a seizure disorder.

Classes of neuropharmaceutical agents which can be used in this invention include antimicrobial agents, antiparasitic agents, agents that act on the autonomic nervous system including adrenergic agents and catecholaminergic agents, anticonvulsants, nucleoside analogues, antineoplastic agents, anti-trauma agents, excitatory amino acids and other classes of agents used to treat or prevent a neurological disorder. Examples of antibiotics include amphotericin B, gentamicin sulfate, pyrimethamine, clindamycin and penicillin. An example of an adrenergic agent (including blockers) is atenolol. Examples of catecholaminergic agents include dopamine, diacetyldopamine and domperidone. Examples of antineoplastic agents include Adriamycin, methotrexate, cyclophosphamide, etoposide, carboplatin and cisplatin. An example of an anticonvulsant which can be used is valproate. Examples of anti-trauma agents which can be used include calpain inhibitors, channel blockers, glutamate chelators and oxygen radical scavengers. Nucleoside analogues which can be used include azido thymidine (AZT), dideoxyinosine (ddI) and dideoxycytidine (ddC).

The molecules in the host's bloodstream can also be diagnostic imaging or contrast agents. Examples of diagnostic agents include substances that are labelled with radioactivity, such as $^{99m}$Tc glucoheptonate, or substances used in Magnetic Resonance Imaging (MRI) procedures such as Gadolinium doped chelation agents (e.g. Gd-DTPA).

The route of administration of exogenous molecules to the host's bloodstream can be parenterally by subcutaneous, intravascular (including intravenous), or intramuscular injection or by absorption through a bodily tissue, such as the digestive tract, the respiratory system or the skin. The dosage form of the molecule (e.g., capsule, tablet, solution, emulsion) will depend, at least in part, on the route by which it is administered.

The administration of the exogenous molecule and the permeabilizer A-7 or conformational analogue to the host's bloodstream can occur simultaneously or sequentially in time. For example, a therapeutic drug can be administered orally in tablet form while the intravenous administration of the permeabilizer A-7 or conformational analogue is performed later (e.g. 30 minutes). This is to allow time for the drug to be absorbed from the gastrointestinal tract and taken up by the bloodstream before the permeabilizer A-7 or conformational analogue is given to increase the permeability of the blood-brain barrier to the drug. On the other hand, the permeabilizer A-7 or conformational analogue can be administered before, after or at the same time as an intravascular injection of a drug. Thus, the term "co-administration" is used herein to mean that the permeabilizer A-7 or conformational analogues and the exogenous molecule will be administered at times that will achieve significant concentrations in the blood for producing the simultaneous effects of increasing the permeability of the blood-brain barrier to the exogenous molecule and allowing the maximum passage of the exogenous molecule from the blood to the interstitial fluid of the brain.

In addition, the molecule to be delivered to the brain via the host's bloodstream can be endogenous to the host. That is, it can be a biological product that is naturally synthesized and produced by the host. Examples of such biological products include sugars, such as glucose, and small peptides, such as enkephalins and thyroid stimulating hormone releasing factor.

An effective amount of the permeabilizer A-7 or conformational analogue is that amount which will significantly increase the blood-brain barrier permeability for the molecule(s) of interest. In other words, it will increase the permeability of the blood-brain barrier to allow sufficient quantities of a molecule of interest to pass from the blood to the interstitial fluid of the brain where it can exert a therapeutic or prophylactic effect or allow for conduct of diagnostic procedures. The effective amount will be determined on an individual basis and will be based, at least in part, on consideration of the individual's size, the specific disease, the severity of symptoms to be treated, the result sought, the specific permeabilizer A-7 or conformational analogue and other variations among hosts, etc. Thus, the effective amount can be determined by one of ordinary skill in the art employing such factors and using no more than routine experimentation.

The increase in permeability of the blood-brain barrier in response to the permeabilizer A-7 or conformational analogue relates not only to the quantity of molecules passing from the blood to the brain, but also, to the type of molecule(s) of interest. The effect of the permeabilizer A-7 or conformational analogue is to preferentially increase the passage of small molecular weight substances through the blood-brain barrier.

The invention is further illustrated by the following specific examples.

EXAMPLE I

Synthesis of the BOC-4-MeTyr $\psi(CH_2N[Z])$Arg (Tos)-O-Resin

N-BOC-O-Methyl-L-Tyrosine N-Methoxy-N-Methylamide

To 350 ml of anhydrous THF on ice was added 3.635 g (37.2 mmol) of N,O-dimethylhydroxylamine hydrochloride. The mixture was stirred for 10 minutes to allow most of the N,O-dimethylhydroxylamine hydrochloride to dissolve. Then, the following ingredients were successively added to the flask: 10 g (33.8 mmol) of N-BOC-O-methyl-L-tyrosine, 6.977 g (33.8 mmol) of dicyclohexylcarbodiimide, 1.96 g (16.04 mmol) of 4-dimethylaminopyridine, and 6.209 ml (35.64 mmols) of N,N-diisopropylethylamine. When all of the reagents had been added, the reaction flask was placed in a cold room (4° C.) and stirred for 12 hours. The contents of the flask were gravity filtered using Whatman Qualitative #1 filter paper. The filtrate was concentrated by means of a rotary evaporator to viscous oil which was then redissolved in 200 mls of methylene chloride. This crude reaction mix was allowed to sit at 4° C. for one hour and then filtered as before in order to remove any residual dicyclohexylurea. The filtrate was again concentrated by means of a rotary evaporator and redissolved in 50 ml of methylene chloride in preparation for column chromatography. Column chromatography was performed using silica (230–400 mesh, 60A) as the adsorbent and 50/50 ethyl acetate/hexane as the eluent. The column used for this scale reaction was 70 cm in length and 10 cm in diameter. The product eluted after approximately 400 ml of eluent had been run through the column. The fractions were all checked by TLC using Silica Gel 60 F-254 glass backed plates. The desired product (Rf value of 0.46) was pooled and concentrated in vacuo. Concentration afforded clear, colorless oil which was placed under high vacuum for several hours. At the end of this time the product remained as a semi-solid material and with time became completely solid.

There remained 5.73 g (50.2%) of a white solid with a mp of 58°–62° C.; IR (cm$^{-1}$, KBr) 3320, 2980, 2840, 1710, 1655, 1520, 1205, 1180; MS m/e 338.4 (M+); $^1$H (CDCl$_3$, 300 MHz) $\delta$7.08 (d,2H, J=8.50 Hz), $\delta$6.82 (d, 2H, J=8.50 Hz), $\delta$5.15 (br d, 1H, J=8.90 Hz), $\delta$4.89 (br m, 1H), $\delta$3.78 (s, 3H), $\delta$3.66 (s, 3H), $\delta$3.17 (br s, 3H), $\delta$2.99 (d of d, 1H, J=6.0 Hz), $\delta$2.83 (d of d, 1H, J=6.0 Hz), $\delta$1.39 (s, 9H); Anal. Calc'd; C, 60.35; H, 7.69; N, 8.28. Found: C, 60.58; H, 8.02; N, 8.31.

N(t-BOC)-O-Methoxy-L-Tyrosinal:

To 150 ml of anhydrous ethyl ether was added 1.04 g (27.37 mmol) of lithium aluminum hydride and the suspension was gently refluxed for 30 minutes. Upon cooling to 4° C., the reflux condenser was replaced by a pressure equalizing dropping funnel containing 7.4 g (21.9 mmol) of N-(t-BOC)-O-methyl-L-tyrosine N-methoxy-N-methylamide dissolved in 100 ml of anhydrous ethyl ether. The contents of the funnel were added over one hour. The reaction mix was allowed to react for an additional two hours. At the end of this time a cold solution of KHSO$_4$ (5.433 g in 230 ml of H$_2$O) was added to the reaction vessel. The layers were separated and the aqueous layer was extracted three times with 150 mls of ether each time. The ether layers were combined and worked up as follows. Washed three times with 200 mls of 3N HCl. Washed three times with 200 mls of saturated sodium bicarbonate. Washed three times with 200 mls of brine. Dried over magnesium sulfate, filtered, and concentrated in vacuo. There remained 3.78 g (61.6%) of a white solid with amp of 69°–72° C.: Rf=0.65 in 50/50 ethyl acetate/hexane; IR (cm$^{-1}$, KBr) 3360, 2840, 1740, 1695, 1530, 1255, 1180: MS m/e 279.3 (M+); $^1$H (CDCl$_3$, 300 MHz) $\delta$9.63 (s, 1H), $\delta$7.08 (d, 2H, J=8.5 Hz) $\delta$6.84 (d, 2H, J=8.5), $\delta$5.05 (br s, 1H), $\delta$4.40 (m, 1H), $\delta$3.79 (s, 3H), $\delta$3.06 (d, 2H, J=6.50), $\delta$1.44 (s, 9H); $^{13}$C NMR (CDCl$_3$, 75.47 MHz) $\delta$200, 158.79, 130.28, 127.69, 114.27, 61.05, 55.29, 34.70, 28.26; Anal. Calc'd: C, 64.51; H, 7.52; N, 5.01. Found: C,64.60; H, 7.86; N, 4.93.

N-BOC-4MeTyr $\psi(CH_2NH)$Arg(Tos)-OH

To a flask containing 100 ml of Methanol:Acetic Acid (99:1) was added 4.92 g (15 mmol) of N$^g$-Tosyl-arginine followed by 1.15 g (18 mmol) of sodium cyanoborohydride. The reagents were stirred for 5 minutes followed by the addition of 4.46 g of N-BOC-4-Me-Tyrosinal. After 30 minutes, an additional 1.15 g (18 mmol) of sodium cyanoborohydride was added to the reaction vessel. Three additional portions of sodium cyanoborohydride were added at thirty minute intervals and the reaction was allowed to stir overnight. The reaction was worked-up by evaporating the solvent. The residue was dissolved in heptane and dried followed by dissolution in ether and drying. Water (200 ml) was added to the flask and the solid collected by filtration. TLC analysis revealed a homogenous product with an Rf of 0.35 (CHCl$_3$: MeOH,4:1). NMR was consistent with the expected product.

N-BOC-4MeTyr ψ(CH$_2$N[Z])Arg(Tos)-OH

To 2.14 g (3.61 mmol) of the pseudodipeptide above was added 1.65 g (19.6 mmol) of NaHCO$_3$ in 100 ml of 1:1 dioxane/water. Benzyl chloroformate (0.6 ml, 4 mmol) was added and the reaction was stirred overnight. The solvents were removed in vacuo leaving a gummy residue. The residue was suspended in 100 ml of water and this was acidified to pH2 with HCl and extracted three times with ethyl acetate. The combined ethyl acetate fractions were dried over magnesium sulfate, filtered and evaporated to provide 2.35 g (90%) of the desired material as a crude amorphous white solid. Recrystallization from methylene chloride/hexane provided 2.18 g (83%) of the product as a white solid. TLC analysis revealed a homogeneous product with an Rf of 0.64 (CHCl$_3$: MeOH, 4:1).

Attachment of the Protected Pseudodipeptide to the Polystyrene Resin

The protected pseudodipeptide was attached to hydroxymethyl resin (Polystyrene-1% Divinylbenzene, 0.7 mequiv./g) using dicyclohexylcarbodiimide and 4-dimethylaminopyridine. To 1.87 g of hydroxymethyl resin (1.31 mmol) was added 2.28 g (3.28 mmol) of the protected pseudodipeptide, 410 mg (3.33 mmol) of 4-dimethylaminopyridine, and 25 ml of anhydrous dimethylformamide in a 50 ml polypropylene tube. To this was added 680 mg (3.3 mmol) of dicyclohexylcarbodiimide and the vessel was shaken overnight at room temperature. The resin was collected by filtration and washed successively three times each with methylene chloride and methanol and dried overnight in vacuo to provide 2.6 g of resin. Substitution by weight gain was calculated to be 0.54 mmol/g.

EXAMPLE II

Synthesis and Purification of Permeabilizer A-7

Permeabilizer A-7 was prepared by solid-phase peptide synthesis by sequentially assembling the remaining amino acids (in a C- to N-fashion) onto the resin bound protected pseudodipeptide. The peptide was synthesized on a Beckman 990 peptide synthesizer using the following program for each coupling cycle: 1—Wash, CH$_2$Cl$_2$ (3×1 min); 2—Deprotect, 40% TFA/CH$_2$Cl$_2$ (2×10 minutes); 3—Wash, CH$_2$Cl$_2$ (3×1 min); 4—Wash, Isopropanol (2×1 min); 5—Wash, CH$_2$Cl$_2$ (3×1 min); 6—Neutralize, 5% DIEA/CH$_2$Cl$_2$(3×2 min); 7—Wash, CH$_2$Cl$_2$ (5×1 min); 8—Couple, (3 equivalents BOC-Amino acid, 3 equivalents of BOP) 1×60 min; 9—Wash, CH$_2$Cl$_2$ (3×1 min); 10—Wash, Isopropanol (2×1 min); 11—Wash, CH$_2$Cl$_2$ (3×1 min); 12—Test for coupling by ninhydrin. If recoupling was necessary as judged by a positive ninhydrin test, a partial cycle starting at step 6 and continuing to the end was done. Following assembly of the complete protected peptide, the N-terminal BOC group was removed by using steps 1–5 in the cycle and the resin dried.

The crude peptide was isolated from the resin by treatment of the protected peptide-resin with anhydrous HF containing 10% anisole for 1 hour at 0° C. The HF was removed in vacuo and the crude resin/peptide was washed with ether three times. The peptide was extracted with 10% acetic acid and lyophilized to yield a crude peptide.

The peptide was partially purified by HPLC using a 0.1% TFA/acetonitrile gradient (10–40% over 30 minutes) on a C$_{18}$ reverse phase support. The fractions from the main peak were combined to provide purified permeabilizer A-7 which appeared homogeneous by TLC, Electrophoresis, and HPLC. FAB/MS analysis yielded the expected MW of 1098. Amino acid analysis after 6N HCl hydrolysis (24 hours at 110° C.) gave the following composition: Ser(1)0.89, Pro (2)2.00, Gly (1)0.97, Arg (1)1.03, Thi(1)0.73. 4Me-Tyr-ψ (CH$_2$NH)-Arg(1) was detected by an alternate method, but was partially destroyed in hydrolysis.

EXAMPLE III

Alternate Synthesis and Purification of Permeabilizer A-7

Permeabilizer A-7 can also be prepared by solid-phase peptide synthesis by sequentially assembling the remaining amino acids (in a C- to N-fashion) starting with a BOC-Arg (Tos)-resin support. The reduced dipeptide was prepared on the support using the following program cycle: 1) Wash, CH$_2$Cl$_2$(3×1 min); 2) Deprotect, 40% TFA/CH$_2$Cl$_2$(1×1 minute, then 1×30 minutes); 3) Wash, CH$_2$Cl$_2$(3×1 min); 4) Wash, Methanol (2×1 min); 5) Wash, CH$_2$Cl$_2$ (3×1 min); 6) Wash, DMF (2×1 min); 7) Wash, DMF/1% HOAc (1×1 min); 8) Couple BOC-4-Me-Tyrosinal. (Note: Three equivalents of BOC-4-Me-Tyrosinal and three equivalents of sodium cyanoborohydride were predissolved in a minimal amount of DMF. To initiate coupling, the amino acid/borohydride solution was added to the washed peptide resin which had been suspended in DMF/1% HOAc.) Coupling was monitored by ninhydrin test and typically found to be complete within thirty minutes. Following the reductive amination, the peptide resin was washed with DMF, then methanol. The secondary amine of the reduced dipeptide was then protected for further synthesis by using a benzyloxycarbonyl group (Z-). This group was introduced by treating the resin with 2×5 equivalents of Z-OSu in 5% DIEA/CH$_2$Cl$_2$ for 1–4 hours each step.

The remaining amino acids were added in a stepwise fashion using the following automated protocol: 1) Wash, CH$_2$Cl$_2$ (3×1 min); 2) Deprotect, 40% TFA/CH$_2$Cl$_2$ (1×1 minute, then 1×30 minutes); 3) Wash, CH$_2$Cl$_2$ (3×1 min); 4) Wash, Methanol (2×1 min); 5) Wash, CH$_2$Cl$_2$ (3×1 min); 6) Neutralize, 5% DIEA/CH$_2$Cl$_2$; 7) Wash, CH$_2$Cl$_2$ (1×1 min); 8) Neutralize, 5% DIEA/CH$_2$Cl$_2$; 9) Wash, CH$_2$Cl$_2$ (3×1 min); 10) Couple (3 equivalents of BOC-Amino acid, 3 equivalents BOP reagent, 3 equivalents of DIEA) for 30 minutes to 2 hours; 11) Wash, MeOH (2×1 minute); 12) Test for coupling by ninhydrin. If recoupling was necessary as judged by a positive ninhydrin test, a partial cycle starting at step 8 and continuing to the end was done. Thus, the following sequence of amino acids were added: BOC-Proline, BOC-Ser(Bz), BOC-Thi, BOC-Gly, BOC-Hyp(Bz), BOC-Pro; BOC-Arg(Tos). Following assembly of the complete protected peptide, the N-terminal BOC group was removed by using steps 1–5 in the cycle and the resin was dried.

The crude peptide was isolated from the resin by treatment of the protected peptide-resin with anhydrous HF containing 10% anisole for 1 hour at 0° C. The HF was removed in vacuo and the crude resin/peptide was washed with ether three times. The peptide was extracted with 10% acetic acid and lyophilized to yield a crude peptide.

The peptide was purified by HPLC using a 0.1% TFA/acetonitrile gradient (0–25% over 180 minutes) on a C$_{18}$ reverse phase support. The fractions from the main peak were combined to provide purified permeabilizer A-7 which appeared homogeneous by TLC, electrophoresis, and HPLC. FAB/MS analysis yielded the expected MW of 1098 and fragmentation pattern which confirmed the proper sequence of permeabilizer A-7.

EXAMPLE IV

Synthesis and Purification of Permeabilizer A-9

Permeabilizer A-9, which is an analogue of permeabilizer A-7 that has dehydroproline rather than proline residues at positions 2 and 7 of the permeabilizer A-7 amino acid sequence ([dehydro Pro$^{2,7}$]-A-7), was prepared by using solid-phase peptide synthesis by sequentially assembling the remaining amino acids (in a C- to N-fashion) starting with a BOC-Arg(Tos)-resin support. The reduced dipeptide was prepared on the support using the following program cycle: 1) Wash, $CH_2Cl_2$ (3×1 min); 2) Deprotect, 40% TFA/$CH_2Cl_2$ (1×1 minute, then 1×30 minutes); 3) Wash, $CH_2Cl_2$ (3×1 min); 4) Wash, Methanol (2×1 min); 5) Wash, $CH_2Cl_2$ (3×1 min); 6) Wash, DMF (2×1 min); 7) Wash, DMF/1% HOAc (1×1 min); 8) Couple, BOC-4-Me-Tyrosinal. (Three equivalents of BOC-4-Me-Tyrosinal and three equivalents of sodium cyanoborohydride were predissolved in a minimal amount of DMF. To initiate coupling, the amino acid/cyanoborohydride solution was added to the washed peptide resin which had been suspended in DMF/1% HOAc). Coupling was monitored by ninhydrin test and typically found to be complete within one hour. Following the reductive amination, the peptide resin was washed with DMF, then methanol. The secondary amine of the reduced dipeptide was then protected for further synthesis using a benzyloxycarbonyl group (Z-). This group was introduced by treating the resin with 2×5 equivalents of Z-Cl in 5% DIEA/$CH_2Cl_2$ for 1–4 hours each step.

The remaining amino acids were added in a stepwise fashion using the following automated protocol: 1) Wash, $CH_2Cl_2$ (3×1 min); 2) Deprotect, 40% TFA/$CH_2Cl_2$ (1×1 minute, then 1×30 minutes); 3) Wash, $CH_2Cl_2$ (3×1 min); 4) Wash, Methanol (2×1 min); 5) Wash, $CH_2Cl_2$ (3×1 min); 6) Neutralize, 5% DIEA/$CH_2Cl_2$; 7) Wash, $CH_2Cl_2$ (1×1 min); 8) Neutralize, 5% DIEA/$CH_2Cl_2$; 9) Wash, $CH_2Cl_2$ (3×1 min); 10) Couple, (3 equivalents of BOC-Amino acid, 3 equivalents BOP reagent, 3 equivalents of DIEA) for 30 minutes to 2 hours; 11) Wash, MeOH (2×1 min); 12) Test for coupling by ninhydrin. If recoupling was necessary as judged by a positive ninhydrin test, a partial cycle starting at step 8 and continuing to the end was done. Thus, the following sequence of amino acids were added: BOC-dehydroProline, BOC-Ser(Bz), BOC-Thi, BOC-Gly, BOC-Hyp(Bz), BOC-dehydroProline, BOC-Arg(Tos). Following assembly of the complete protected peptide, the N-terminal BOC group was removed by using steps 1–5 in the cycle and the resin was dried.

The crude peptide was isolated from the resin by treatment of the protected peptide-resin with anhydrous HF containing 10% anisole for 1 hour at 0° C. The HF was removed in vacuo and the crude resin/peptide was washed with ether three times. The peptide was extracted with 10% acetic acid and lyophilized to yield a crude peptide.

The peptide was purified by HPLC using a 0.1% TFA/acetonitrile gradient (0–25% over 180 minutes) on a $C_{18}$ reverse phase support. The fractions from the main peak were combined to provide purified permeabilizer A-9 which appeared homogeneous by TLC, Electrophoresis, and HPLC. Amino acid analysis yielded the following results: Ser(1) 0.97, dehydroPro(2) 1.69, Gly(1) 0.95, Arg(1) 0.95, Hyp(1) 0.92, Thi(1) 0.75.

EXAMPLE V

Synthesis and Purification of Permeabilizer A-14

Permeabilizer A-14, which is permeabilizer A-7 to which a D-arginine has been attached to the N-terminus by a peptide bond, i.e. [D-Arg$^0$]-A-7, was prepared by solid-phase peptide synthesis by sequentially assembling the remaining amino acids (in a C- to N-fashion) starking with a BOC-Arg(Tos)-resin support. The reduced dipeptide was prepared on the support using the following program cycle: 1) Wash, $CH_2Cl_2$ (3×1 min); 2) Deprotect, 40% TFA/$CH_2Cl_2$ (1×1 minute, then 1×30 minutes); 3) Wash, $CH_2Cl_2$ (3×1 min); 4) Wash, Methanol (2×1 min); 5) Wash, $CH_2Cl_2$ (3×1 min); 6) Wash, DMF (2×1 min); 7) Wash, DMF/1% HOAc (1×1 min); 8) Couple BOC-4-Me-Tyrosinal. (Note: Three equivalents of BOC-4-Me-Tyrosinal and three equivalents of sodium cyanoborohydride were predissolved in a minimal amount of DMF. To initiate coupling, the amino acid/borohydride solution was added to the washed peptide resin which had been suspended in DMF/1% HOAc.) Coupling was monitored by ninhydrin test and typically found to be complete within thirty minutes. Following the reductive amination, the peptide resin was washed with DMF, then methanol. The secondary amine of the reduced dipeptide was then protected for further synthesis by using a benzyloxycarbonyl group (Z-). This group was introduced by treating the resin with 10% benzylchloroformate in 5% DIEA/$CH_2Cl_2$ for 30 minutes. The resin was then washed with $CH_2Cl_2$ (3×1 min), ethanol (1×1 min) and $CH_2Cl_2$ (3×1 min).

The remaining amino acids were added in a stepwise fashion using the following automated protocol: 1) Wash, $CH_2Cl_2$ (3×1 min); 2) Deprotect, 40% TFA/$CH_2Cl_2$ (1×1 minute, then 1×30 minutes); 3) Wash, $CH_2Cl_2$ (3×1 min); 4) Wash, Methanol (2×1 min); 5) Wash, $CH_2Cl_2$ (3×1 min); 6) Neutralize, 5% DIEA/$CH_2Cl_2$;7) Wash, $CH_2Cl_2$ (1×1 min); 8) Neutralize, 5% DIEA/$CH_2Cl_2$; 9) Wash, $CH_2Cl_2$ (3×1 min); 10) Couple, (4 equivalents of BOC-Amino acid, 4 equivalents DCC, 4 equivalents of HOBt) for 30 minutes to 2 hours; 11) Wash, MeOH (2×1 min). Arginine was double coupled by repeating step 10 with fresh reagents. Thus, the following sequence of amino acids were added: BOC-Proline, BOC-Ser(Bz), BOC-Thi, BOC-Gly, BOC-Hyp(Bz), BOC-Pro, BOC-Arg(Tos), BOC-D-Arg(Tos). Following assembly of the complete protected peptide, the N-terminal BOC group was removed by using steps 1–5 in the cycle and the resin was dried.

The crude peptide was isolated from the resin by treatment of the protected peptide-resin with anhydrous HF containing 10% anisole for 1 hour at 0° C. The HF was removed in vacuo and the crude resin/peptide was washed with ether three times. The peptide was extracted with 10% acetic acid and lyophilized to yield a crude peptide.

The peptide was partially purified by HPLC using a 0.1% TFA/acetonitrile step gradient (5, 40 and 75% acetonitrile) on a $C_{18}$ reverse phase support. The 40% eluant fraction was further purified using 0.1% TFA/Acetonitrile gradient of 10–20% over 60 minutes on a $C_4$ support. The fractions from the main peak were combined to provide purified permeabilizer A-14 which appeared homogeneous by HPLC. FAB/MS analysis yielded the expected MW of 1155. Amino acid analysis yielded the following results: Hyp (1) 1.02, Ser (1) 0.98, Gly (1) 0.86, Arg (2) 2.07, Pro (2) 2.08.

EXAMPLE VI

Time Course of Blood-Brain Barrier Opening in Mice

Female Balb/C mice weighing approximately 20 g were used. All solutions were prepared in sterile phosphate-buffered saline. An intravenous injection of 10 μg permeabilizer A-7 in 100 μl was given in the tail vein at time=0. Either immediately or at 10, 20, 30, or 60 minutes after the permeabilizer A-7 injection, $^{14}C$ sucrose (3×10$^6$ dpm) was intravenously injected in the tail vein. In some experiments, sucrose was given immediately following permeabilizer A-7 injection, and mice were euthanitized either 2 or 5 minutes later. In other experiments, mice were euthanitized 10 minutes after the $^{14}$C sucrose administration. Blood was collected in heparinized tubes and centrifuged to separate plasma from the resulting pellet. Radioactivity in a 100 μl aliquot of plasma was measured by liquid scintillation counting after the addition of 15 ml of Aquasol-2 (Dupont). The brain was removed and homogenized in 2.5 ml of water and 2.5 ml of 1% sodium dodecyl sulfate (SDS). One ml of the homogenate was aliquoted and added to 15 ml of Aquasol-2 for counting. Brain uptake of sucrose was calculated and graphically expressed as percent of injected dose × 100. As seen in FIG. 1, where the abscissa values represent time intervals between injection of permeabilizer A-7 and euthanasia, the uptake of $^{14}$C-sucrose at 10 and 20 minutes was significantly higher in the presence of permeabilizer A-7. The blood-brain barrier remained permeable to sucrose for at least 20 minutes following injection of permeabilizer A-7 but did not remain permeable after 40 minutes. Each data point represents the mean ± s.d. from 8 mice.

EXAMPLE VII

Time Course of Blood-Brain Barrier Opening in Mice for Permeabilizer A-7 and Two of Its Diastereomers (8D and 9D).

Female Balb/C mice weighing approximately 20 g were used. All solutions were prepared in sterile phosphate buffered saline. Permeabilizer A-7 was compared with two of its diastereomers, 8D-A-7 and 9D-A-7, using the sucrose uptake assay in experiments similar to those described in Example VI. For 8D-A-7, D-4-Me-tyrosine was the starting material for the eighth position amino acid in the peptide produced from solid phase peptide synthesis. For the 9D-A-7 diastereomer, the solid phase resin was esterified with protected D-arginine prior to the synthesis. Saline or various doses of the diastereomers were administered via lateral tail vein injection as a mixture with $^{14}$C-sucrose and ten minutes later the mice were euthanatized. Blood from each animal was collected into individual heparinized tubes and centrifuged to separate plasma from the resulting pellet. Radioactivity in a 20 μL aliquot of plasma was counted by liquid scintillation counting after the addition of 15 mL of Aquasol. The brain was removed and homogenized in 5 mL of a 0.5% sodium dodecyl sulfate solution. Radioactivity in a 1 mL aliquot of this homogenate was counted.

In some experiments, to determine actual uptake into brain tissue of the radiolabelled compound of interest which was induced by permeabilizer A-7, the contribution of radiolabelled compound in blood to the total radioactivity found in brain was estimated. The assumption was made that all radioactivity in control brains was contributed by the radioactivity present in the blood. Thus, by dividing the quantity of radioactivity per control brain by the radioactivity per μL of control blood, a specific value for μL of blood per control brain was obtained. It was then assumed that control and permeabilizer A-7 treated brains contain the same volume of blood. Then, the quantity of blood per control brain was multiplied by the radioactivity per μL blood of permeabilizer A-7-treated mice, and the radioactivity in blood per brain for permeabilizer A-7 treated mice was thereby approximated. Finally, radioactivity in blood contained in the treated brains was subtracted from radioactivity in treated brains to obtain the amount of the radiolabelled substance in permeabilizer A-7 treated brain tissue alone. Brain uptake of sucrose was calculated and expressed as percent of injected dose.

Figure 2:
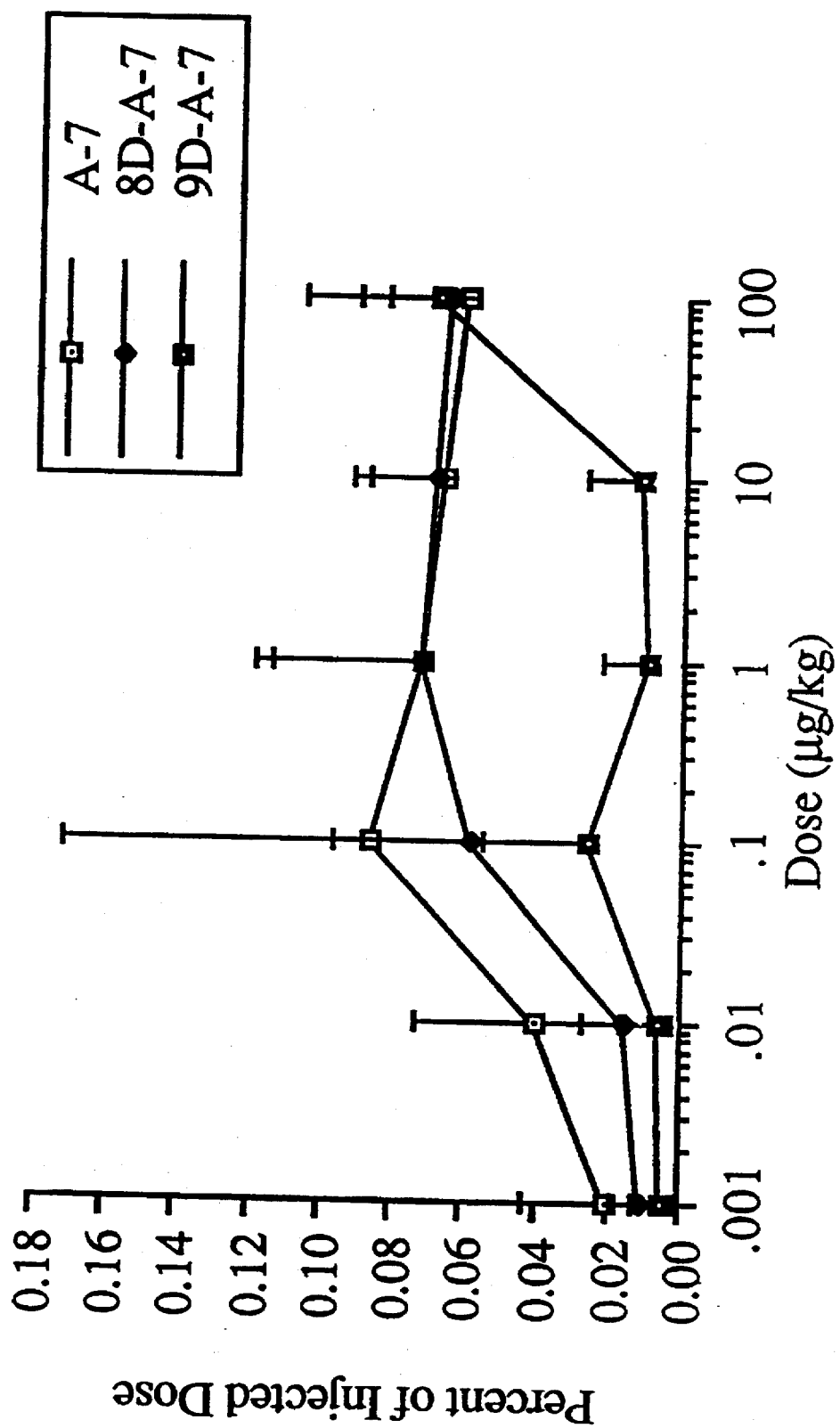
FIG. 2 is a graphic representation of brain uptake of sucrose after the administration of various amounts of permeabilizer A-7 and of two of its diastereomers.

The uptake of $^{14}$C-sucrose in the presence of these diastereomers is shown in FIG. 2. As can be seen from this FIG., the 8D, but not the 9D diastereomer, was about equally active when compared with the permeabilizer A-7 in enhancing $^{14}$C-sucrose uptake into brain.

EXAMPLE VIII

Dose Response Relationship of Bradykinin, Permeabilizer A-7 and Other Blood-Brain Barrier Permeabilizers. Sucrose Uptake Studies The methodology for these experiments is similar to the previously described time course study (Example VI) with the exception that all mice were euthanatized 10 minutes after receiving a single tail vein injection of a mixture of $^{14}$C-sucrose with bradykinin, permeabilizer A-7 or another blood-brain barrier permeabilizers.

Figure 3A:
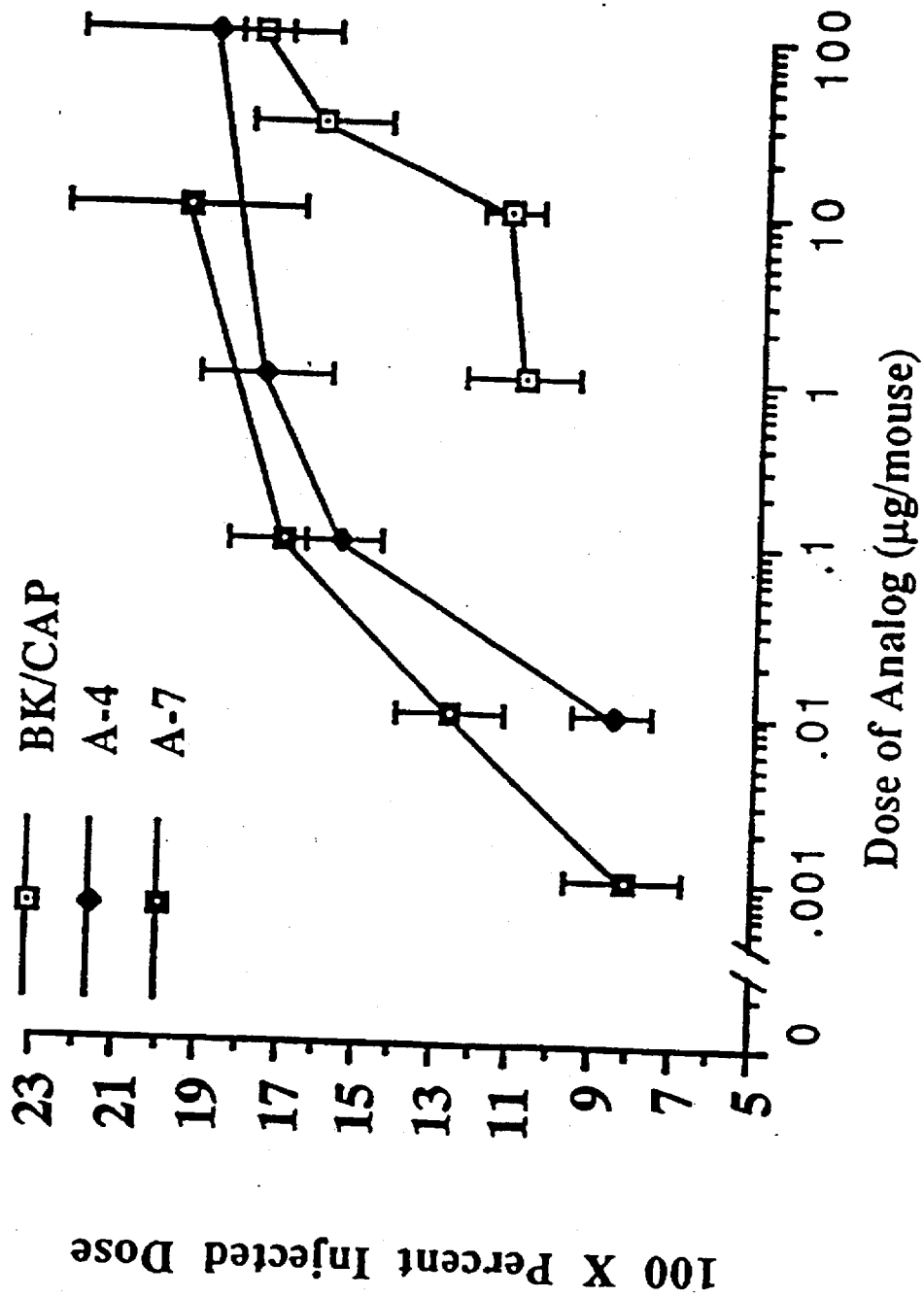
FIG. 3a is a graphic representation of brain uptake of sucrose, displayed as percent of injected dose, following the administration of bradykinin or permeabilizer analogues.
Figure 3B:
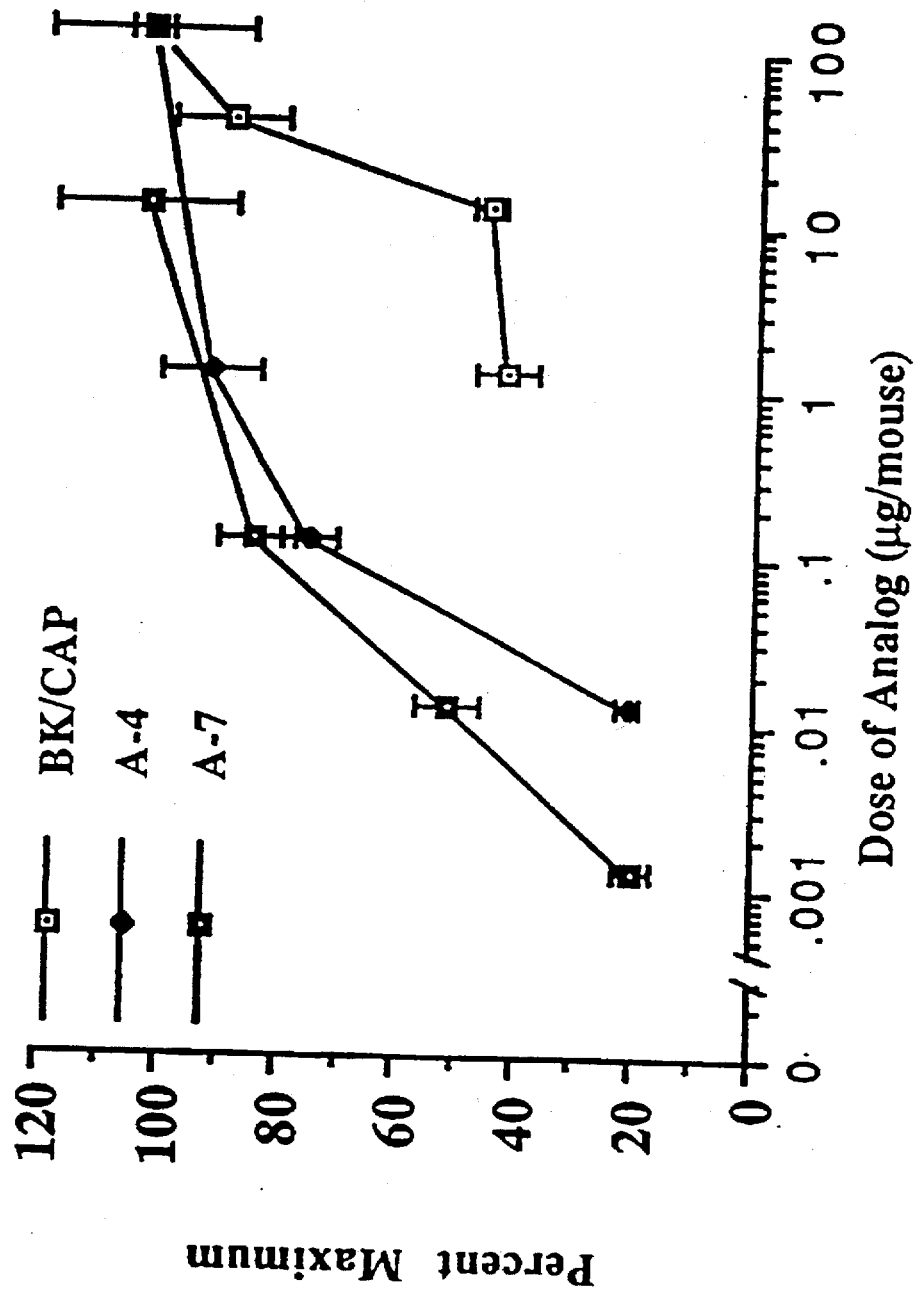
FIG. 3b is a graphic representation of brain uptake of sucrose, displayed as percent of maximum uptake, following the administration of bradykinin or permeabilizer analogues.

FIG. 3a shows the amount of $^{14}$C-sucrose uptake expressed as 100×percent of injected dose for various doses of bradykinin, permeabilizer A-7 or another blood-brain barrier permeabilizer, A-4 ([Thi$^5$, Phe$^8$ ψ(CH$_2$—NH) Arg$^9$]-bradykinin) 10 minutes after the injection. FIG. 3b represents the percent maximum response ($^{14}$C sucrose uptake) over the range of doses of bradykinin, permeabilizer A-7 or permeabilizer A-4. Permeabilizers A-4 and, particularly, A-7 are more potent than the combination of bradykinin and captopril (BK+Cap). The number of mice per data point ranged from 12 to 16.

Figure 3C:
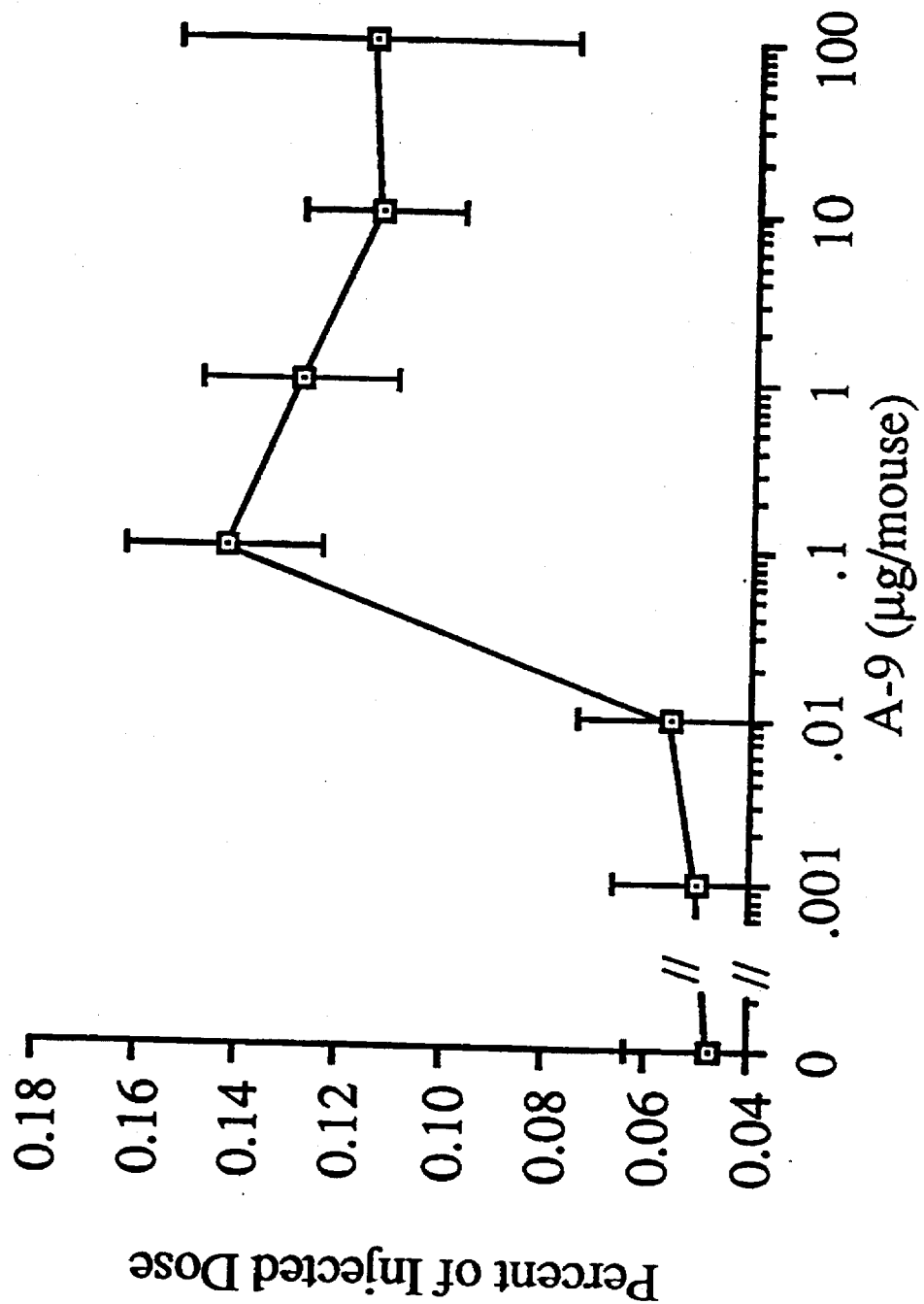
FIG. 3c is a graphic representation of brain uptake of sucrose, displayed as percent of injected dose, following the administration of various amounts of a permeabilizer A-7 analogue, A-9.
Figure 3D:
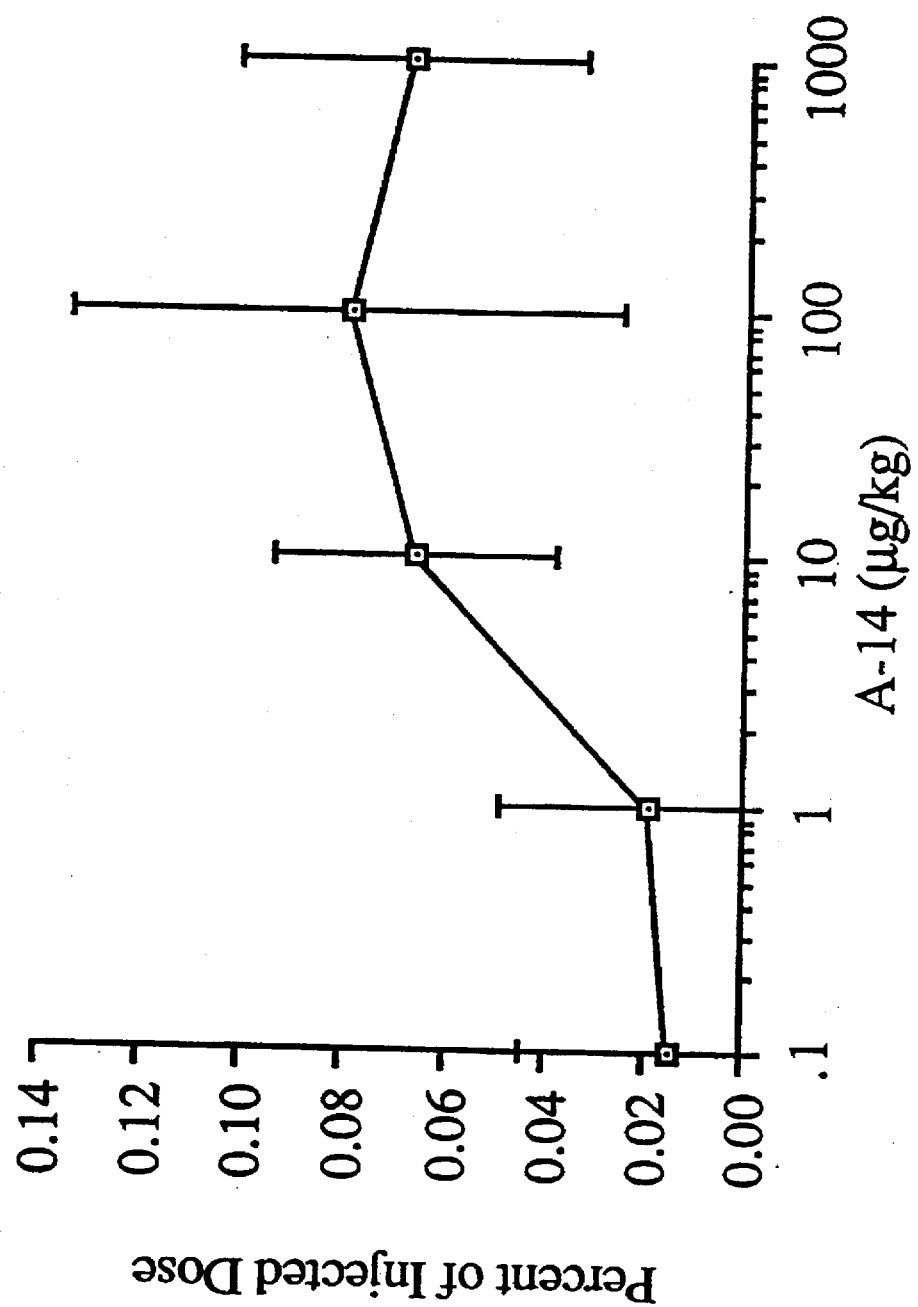
FIG. 3d is a graphic representation of brain uptake of sucrose, displayed as percent of injected dose, following the administration of various amounts of a permeabilizer A-7 analogue, A-14.

Two additional conformational analogues of permeabilizer A-7 were also examined in similar $^{14}$C-sucrose uptake experiments in mice. The results obtained with permeabilizers A-9 [dehydro Pro$^{2,7}$]-A-7) and A-14 ([D-Arg$^0$]-A-7), are shown in FIGS. 3c and 3d, respectively. The two analogues also enhanced the uptake of $^{14}$C-sucrose into the brain in a manner comparable to A-7. Eight mice per time point were used in these studies.

EXAMPLE IX

Uptake of Substances of Different Molecular Weights into the Brain of Mice When Co-administered with Permeabilizer A-7

The methodology of these experiments is similar to that of the above three examples. Specific radioactively labeled molecules of different molecular weight and structure, either with saline or with 1 or 10 μg of permeabilizer A-7 in saline, were intravenously injected into mice via the tail vein. The animals were euthanatized 10 minutes after the co-administration and the radioactivity present in brain was measured as described previously for $^{14}$C sucrose. The results of these studies are shown in Table I.

TABLE I

Uptake of Radiolabelled Substances into the Brain

| Molecule | Mol. Weight | % Injected Dose Control | +10 μg A-7 |
|---|---|---|---|
| $^{14}$C-Sucrose | 342 | 0.059 ± 0.014 | 0.165 ± 0.049 |
| $^{14}$C-Clindamycin | 425 | 0.085 ± 0.051 | 0.140 ± 0.082* |
| $^{3}$H-Inulin | 5,000 | 0.075 ± 0.018 | 0.110 ± 0.016 |
| $^{3}$H-RNase | 12,600 | 0.123 ± 0.039 | 0.117 ± 0.030 |
| $^{3}$H-Myoglobin | 14,000 | 0.092 ± 0.022 | 0.073 ± 0.014 |
| $^{3}$H-Carbonic Anhydrase | 30,000 | 0.090 ± 0.013 | 0.106 ± 0.015 |
| $^{3}$H-Ovalbumin | 46,000 | 0.079 ± 0.016 | 0.093 ± 0.017 |
| $^{3}$H-Bovine Serum Albumin | 68,000 | 0.333 ± 0.098 | 0.209 ± 0.056 |

Data are presented as mean ± s.d. for 7 to 15 mice in each group.
*Permeabilizer A-7 dose was 1 μg.

Additional experiments were conducted using 100 μg/kg of permeabilizer A-7 with compounds of different molecular weights in mice. These experiments incorporated analytical methods (correction for radioactivity in blood) similar to those described in Example VII for the 8D and 9D diastereomers of permeabilizer A-7. The results from these additional experiments are represented in Table II.

TABLE II

Uptake of Radiolabelled Substances into the Brain

| Molecule | Molecular Weight | % Injected Dose 100 μg/kg A-7 |
|---|---|---|
| $^{14}$C-Ethanol | 46 | 0.031 ± 0.260 |
| $^{14}$C-Pyrimethamine | 249 | 0.659 ± 0.412 |
| $^{3}$H-Inulin | 5,000 | 0.075 ± 0.065 |
| $^{14}$C-Dextran | 5,000 | 0.013 ± 0.014 |
| $^{14}$C-Dextran | 8,000 | 0.015 ± 0.017 |
| $^{14}$C-Dextran | 10,000 | 0.00 |

It appears that substances with lesser molecular weights preferentially cross the blood-brain barrier when coadministered with permeabilizer A-7.

EXAMPLE X

The Effect of the Anti-Neoplastic Agent Cisplatin on the Survival Time of Rats with Brain Tumor Implants When Co-administered with Bradekinin or Permeabilizer A-7

Male Fischer 344 rats (200–250 g) were anesthetized with ketamine HCL (100 mg/kg) and acepromazine (10 mg/kg). The animals were placed in a stereotaxic device. The head of each animal was shaved and a midline incision was made to expose the skull. A small hole was drilled over the right sensorimotor cortex. A 100 μl cell suspension (250,000 9L Glioma cells) was injected over 5 minutes into the right caudate putamen of each animal and the scalp sutured. Animals were observed daily for signs of failing health. When signs of very poor health were observed (eye hemorrhage or loss of righting reflex) animals were euthanatized and the brains examined for presence of tumor.

On days 5 through 14, groups of animals received the following intravenous treatments via the tail vein: no treatment; cisplatin 200 μg/rat; 50 μg permeabilizer A-7 followed 5 minutes later by cisplatin; or captopril intraperitoneally followed 15 minutes later by 1 mg bradykinin (BK+Cap), followed by cisplatin 5 minutes after the bradykinin. The results are shown in Table III as median survival with range.

TABLE III

| Treatment Group | Median Survival (days) | No. Animals |
|---|---|---|
| Control | 14, Range 10–16 | 6 |
| Cisplatin | 13, Range 9–18 | 9 |
| BK+Cap + Cisplatin | 16, Range 10–21 | 9 |
| A-7 + Cisplatin | 20.5, Range 10–62 | 9 |

Figure 4A:
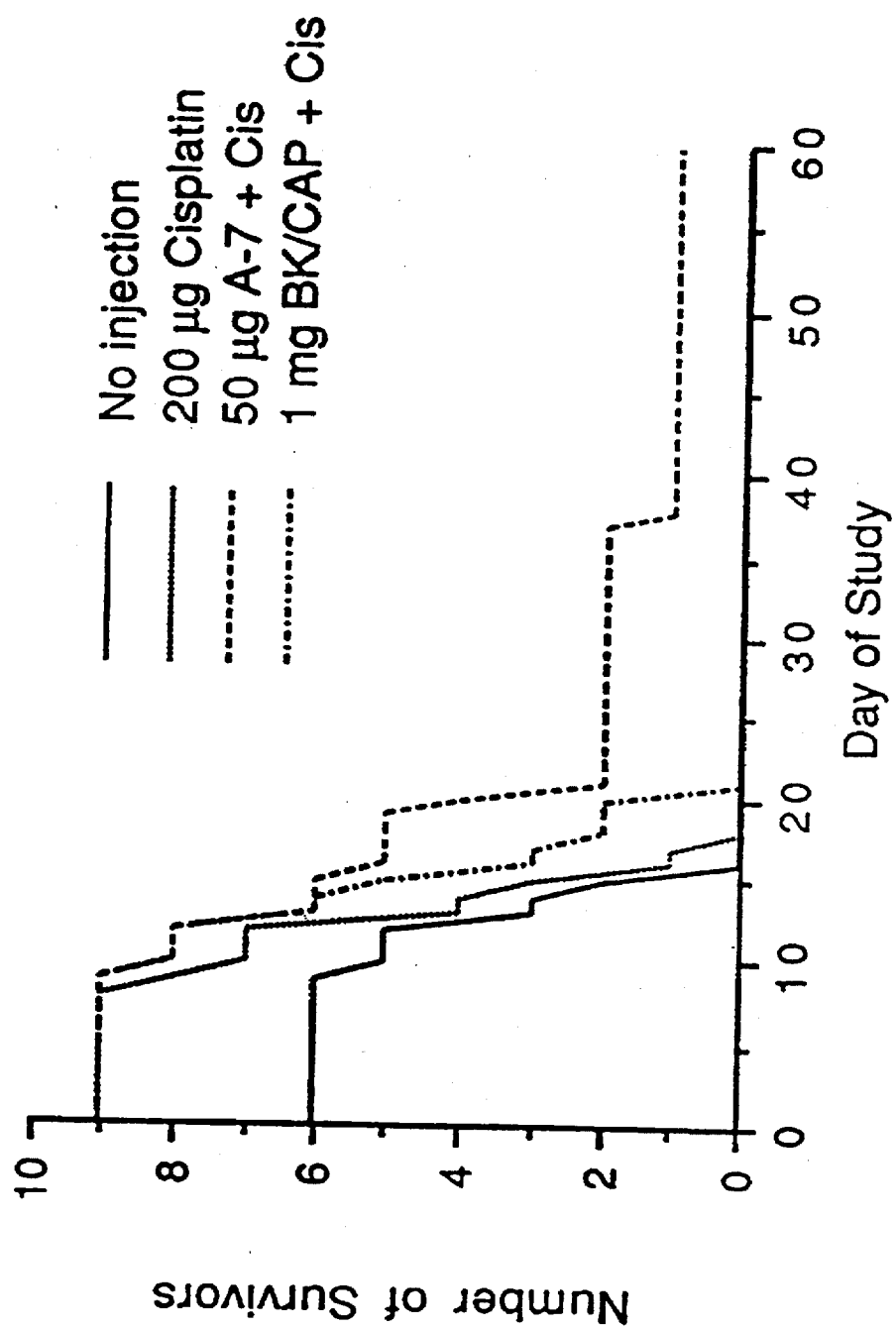
FIG. 4a is a graphic representation of the effects of no treatment; treatment with cisplatin; treatment with bradykinin, captopril and cisplatin; and treatment with permeabilizer A-7 and cisplatin on survival time (days) of rats implanted with a brain tumor.

FIG. 4a illustrates the survival times of all animals in the study. It should be noted that 2 animals in the permeabilizer A-7 + Cisplatin treatment group had extended survival times, with one animal dying on day 38 and the other euthanatized at day 62. Both animals had evidence of tumor growth.

Figure 4B:
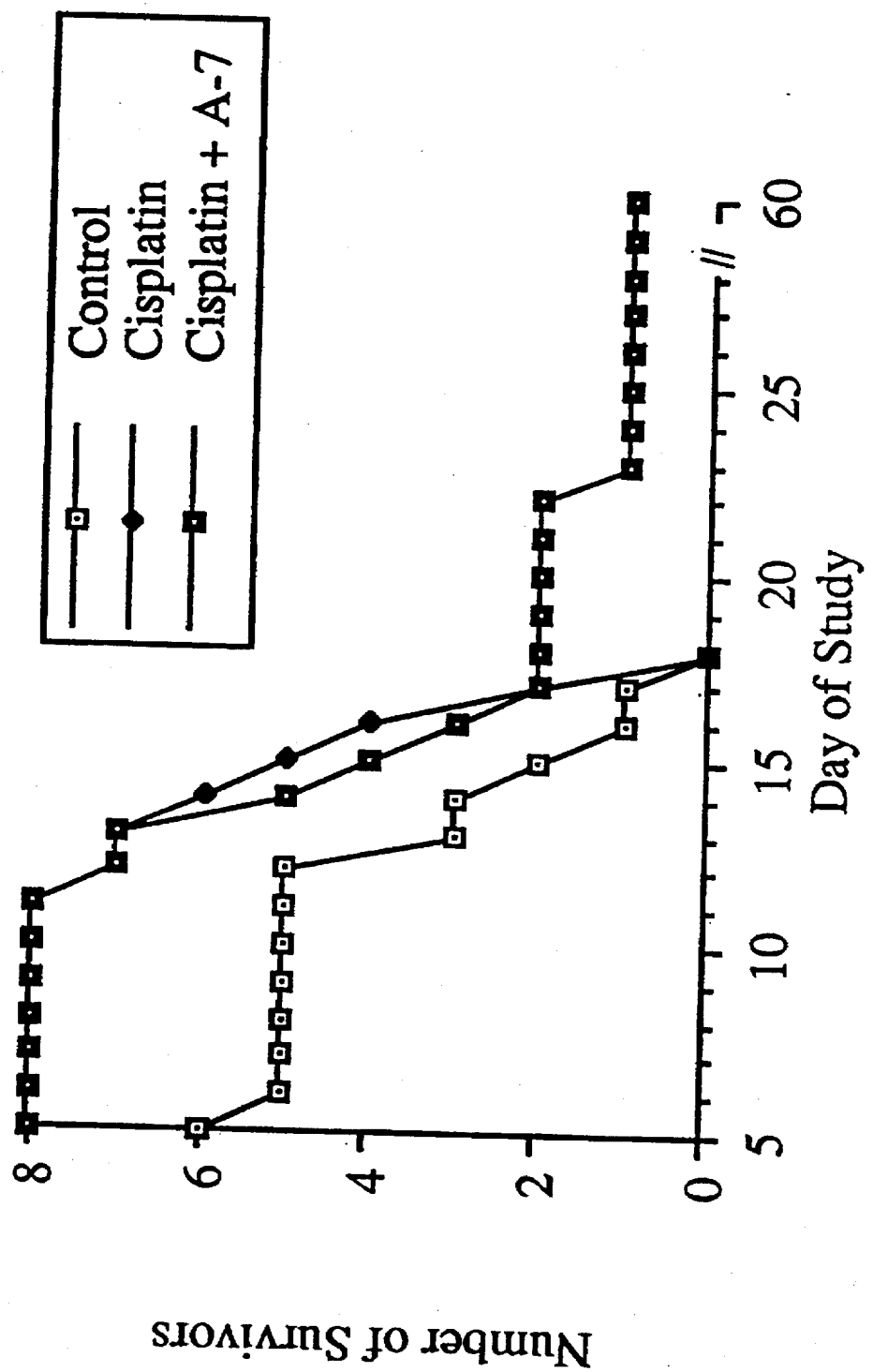
FIG. 4b is a graphic representation of the effects of no treatment; treatment with cisplatin; and treatment with permeabilizer A-7 and cisplatin on survival time in days of rats implanted with a brain tumor.

The results from an additional experiment that was conducted with cisplatin and the permeabilizer A-7 are shown in FIG. 4b and Table IV.

TABLE IV

| Treatment Group | Median Survival (days) | No. Animals |
|---|---|---|
| Control | 13, Range 6–18 | 6 |
| Cisplatin | 15.5, Range 12–18 | 8 |
| A-7 + Cisplatin | 14.5, Range 12–60* | 8 |

*one died on day 23; one died on day 60 (euthanatized)

In this experiment, no increase in median survival time was observed with the combination of permeabilizer A-7 and cisplatin compared to cisplatin alone. However, there were two animals that survived for an extended time period in the combination group.

Figure 5:
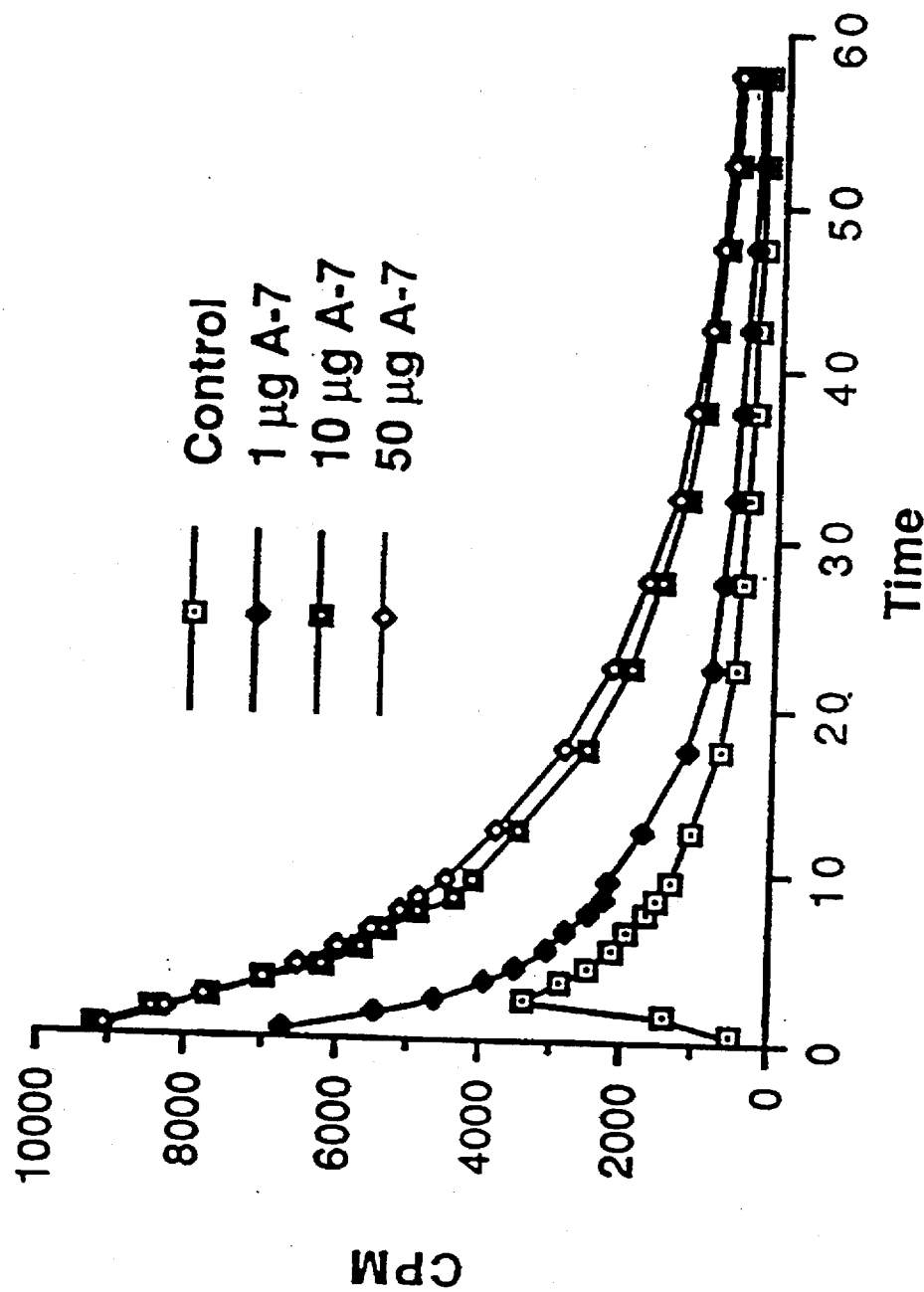
FIG. 5 is a graphic representation of the brain uptake of an imaging agent DISIDA intravenously injected 2 minutes after either saline or one of three different amounts of permeabilizer A-7 was intravenously injected into rats.

EXAMPLE XI $^{99m}$Tc-DISIDA (N-[2,6-Diisopropylacetanilide] iminodiacetec acid) Uptake into the Head Region (Brain) in Rats Female Sprague-Dawley rats (250–300 g) were anesthetized with pentobarbital (60 mg/kg) and ketamine (100 mg/kg). The femoral veins were surgically exposed and the right femoral vein was injected either with saline or with a range of permeabilizer A-7 doses. After two minutes, a bolus dose of $^{99m}$Tc-DISIDA was injected into the left femoral vein. The rats were immediately placed on a gamma camera and the radioactivity counted at 1 minute intervals for the first 5 minutes and then at 5 minute intervals until 1 hour post-DISIDA injection. The head region, where the brain is the primary organ, was identified and the amount of radioactivity present in this region is shown in FIG. 5 for the control and each of the doses of permeabilizer A-7 tested. The data for each dose are radioactivity measurements from a single rat. At very early times, the permeabilizer A-7 enhanced the uptake of $^{99m}$Tc-DISIDA into this region relative to the control animal. This experiment is representative of two similar studies.

Figure 6:
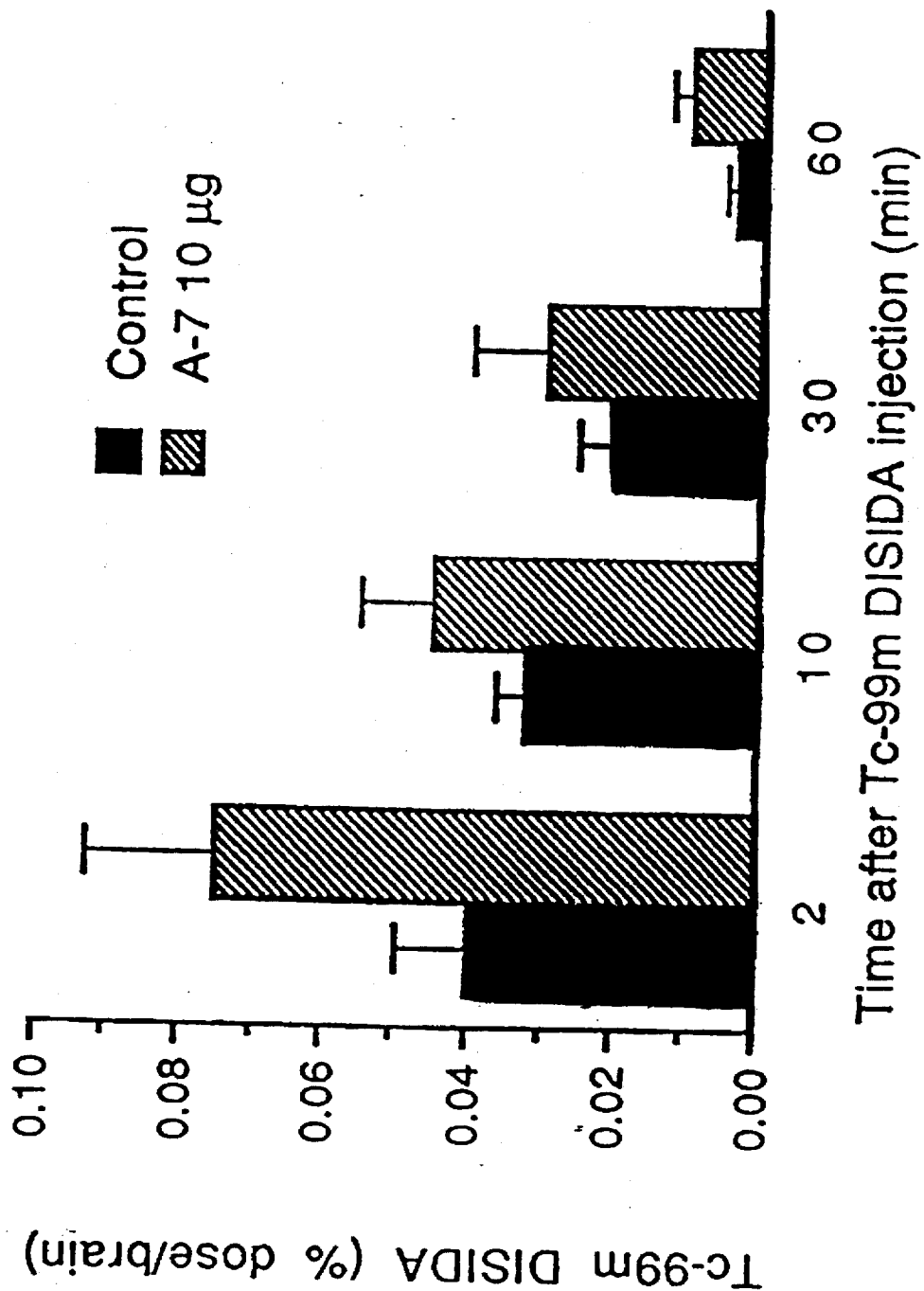
FIG. 6 is a histogram which illustrates the effect of intravenously administered permeabilizer A-7 on the uptake of the imaging agent DISIDA into the brain.

In another set of experiments, a single intravenous injection of permeabilizer A-7 was given into a femoral vein of an anesthetized rat. Two minutes later, an injection of $^{99m}$Tc-DISIDA was given into the contralateral femoral vein. In control animals, no permeabilizer A-7 was injected (sham injection of saline). At time intervals of 2, 10, 30 or 60 minutes after the $^{99m}$Tc-DISIDA injection, the rats were euthanatized, their brains removed and counted in a gamma counter. The brain uptake of $^{99m}$Tc-DISIDA was calculated and expressed as percent of injected dose per organ. The biodistribution of $^{99m}$Tc-DISIDA into the whole brain of untreated and permeabilizer A-7 treated rats at selected times post-injection is shown in Table V and FIG. 6.

TABLE V

Biodistribution of $^{99m}$Tc-DISIDA in Brain

| Time (after $^{99m}$Tc-DISIDA Injection) | % Injected Dose/Brain | |
|---|---|---|
| | Control | + 10 µg RMP-7 |
| 2 min. | 0.040 ± 0.013 | 0.075 ± 0.019 |
| 5 min. | 0.032 ± 0.003 | 0.046 ± 0.006 |
| 10 min. | 0.022 ± 0.005 | 0.028 ± 0.003 |
| 60 min. | 0.004 ± 0.001 | 0.010 ± 0.003 |

The data are expressed as mean ± s.d. for three animals per group.

These results demonstrate that more $^{99m}$Tc-DISIDA is found in the brain of permeabilizer A-7 treated rats when compared to control rats at early times post-injection of the radiolabelled agent.

EXAMPLE XII

The Effect of Permeabilizer A-7 on the Antinociceptive Effect of Loperamide. Tail Flick Assay Female Nalb/C mice weighing approximately 20 g were used. The tail flick assay was performed using a Tail Flick Apparatus model TF6 (Emdie Instruments, Maidens, Va.). The intensity of the heat source was adjusted daily to yield a reaction time between 2.0 and 3.2 seconds in naive untreated mice. The maximum time of exposure to the heat source allowed was 7.5 seconds. The tail withdrawal reaction time of each mouse was measured 4 times at 10 second intervals immediately prior to intravenous injections of the experimental substances via the tail vein. The last three values were averaged and taken as baseline value ($V_o$). Another set of four measurements was taken at the following intervals after tail vein injection of the opiate receptor agonist loperamide with and without the other agents: immediately, 5 min, 10 min, 15 min, 30 min, and 60 min. The last three values for each of these time points (V) were averaged. In some experiments the opiate receptor antagonist nalorphine (10 mg/kg; 100 µl in saline) was administered intraperitoneally 15 minutes prior to administration of permeabilizer A-7 (0.1 µg) and loperamide (25 µg). The results were expressed as percent of maximum antinociceptive response according to the formula: $100 \times (V - V_o)/(7.5 - V_o)$.

Figure 7:
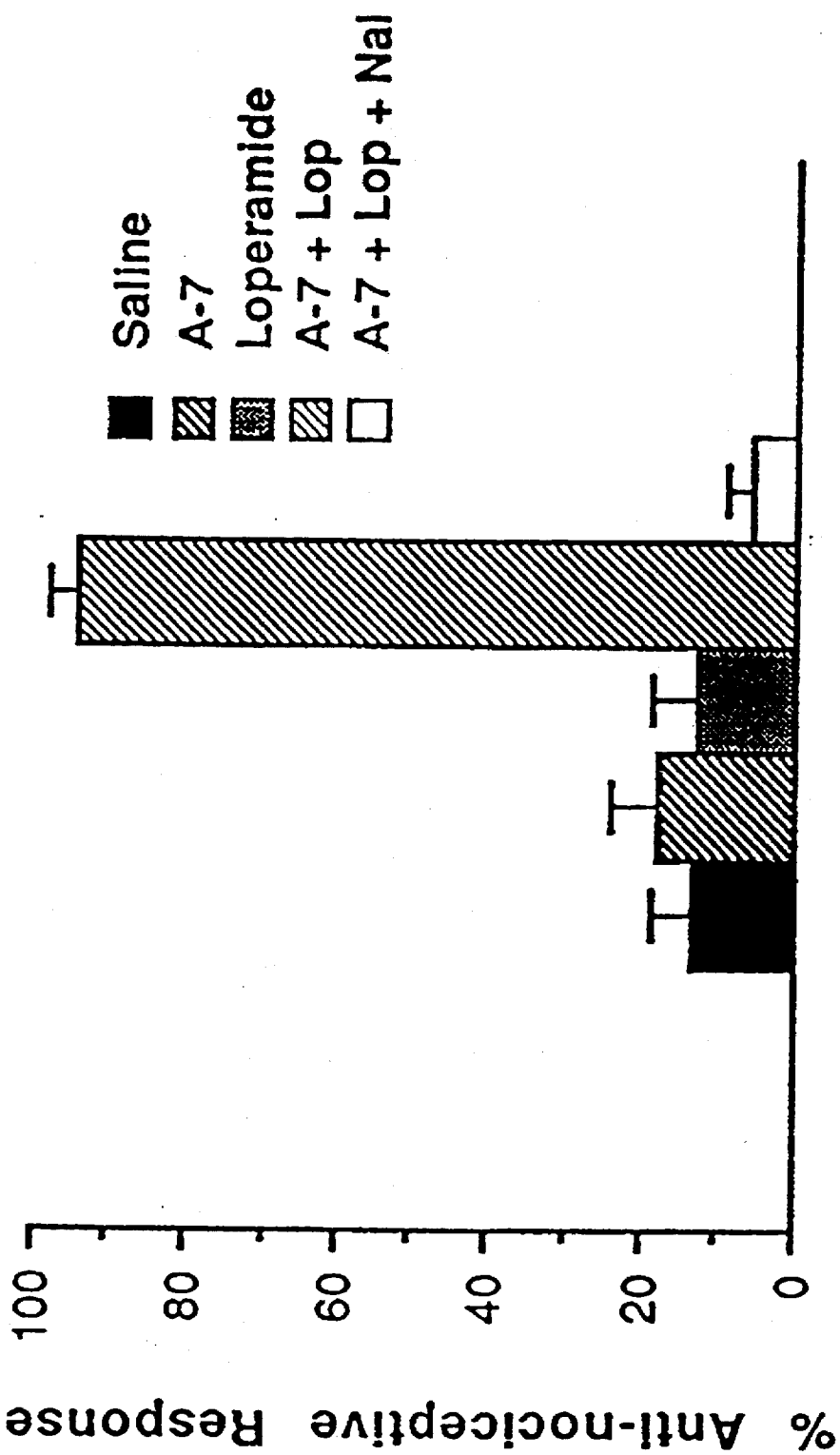
FIG. 7 is a histogram which illustrates the effect of co-administered permeabilizer A-7 on the antinociceptive activity of loperamide in the mouse tail flick assay.

FIG. 7 illustrates the ability of permeabilizer A-7 to enhance the permeability of the blood-brain barrier to loperamide as evidenced by the increase in % maximum antinociceptive response. Each point represents pooled data from 2 experiments with 4 mice (total of 8 mice per point) 30 minutes after injection of loperamide, permeabilizer A-7, and permeabilizer A-7 and loperamide with or without nalorphine pretreatment. A complete antinociceptive response was obtained when permeabilizer A-7 was coinjected with loperamide. The effect was completely antagonized by pretreatment with nalorphine.

EXAMPLE XIII

The Effect of a Dopaminergic Antagonist When Co-administered with Permeabilizer A-7 on the Locomotor Activity of Rats Domperidone is a dopamine receptor antagonist used clinically as an anti-emetic by virtue of its action at the area postrema outside the blood-brain barrier. Reports in the literature have demonstrated that domperidone does not cross the blood-brain barrier, but when given as an injection directly into the cerebral ventricles, it effectively blocks binding of dopaminergic compounds, such as apomorphine, to dopamine receptors. A pertinent test is whether domperidone can antagonize a dopamine receptor agonist-induced increase in motor activity when co-administered with permeabilizer A-7 but is ineffective when administered without permeabilizer A-7.

Sprague-Dawley rats (125–150 g) were habituated for two days to activity cages. The activity cages were standard size rat cages with two photocell beams running across the floor of each cage. Any movement of the rat through either of the beams was recorded by a computer. Locomotor activity was measured as the number of beam breaks in a sequence of 10-minute intervals over a two hour period.

The rats were given a coinjection of 10 µg permeabilizer A-7 and 300 µg domperidone, or the domperidone alone, one hour before a subcutaneous injection of apomorphine (0.75 mg/kg), which is a dopamine agonist that readily crosses the blood-brain barrier. The motor activity of the rats was measured in activity cages over 10-minute intervals for up to 2 hours post-apomorphine injection.

Figure 8:
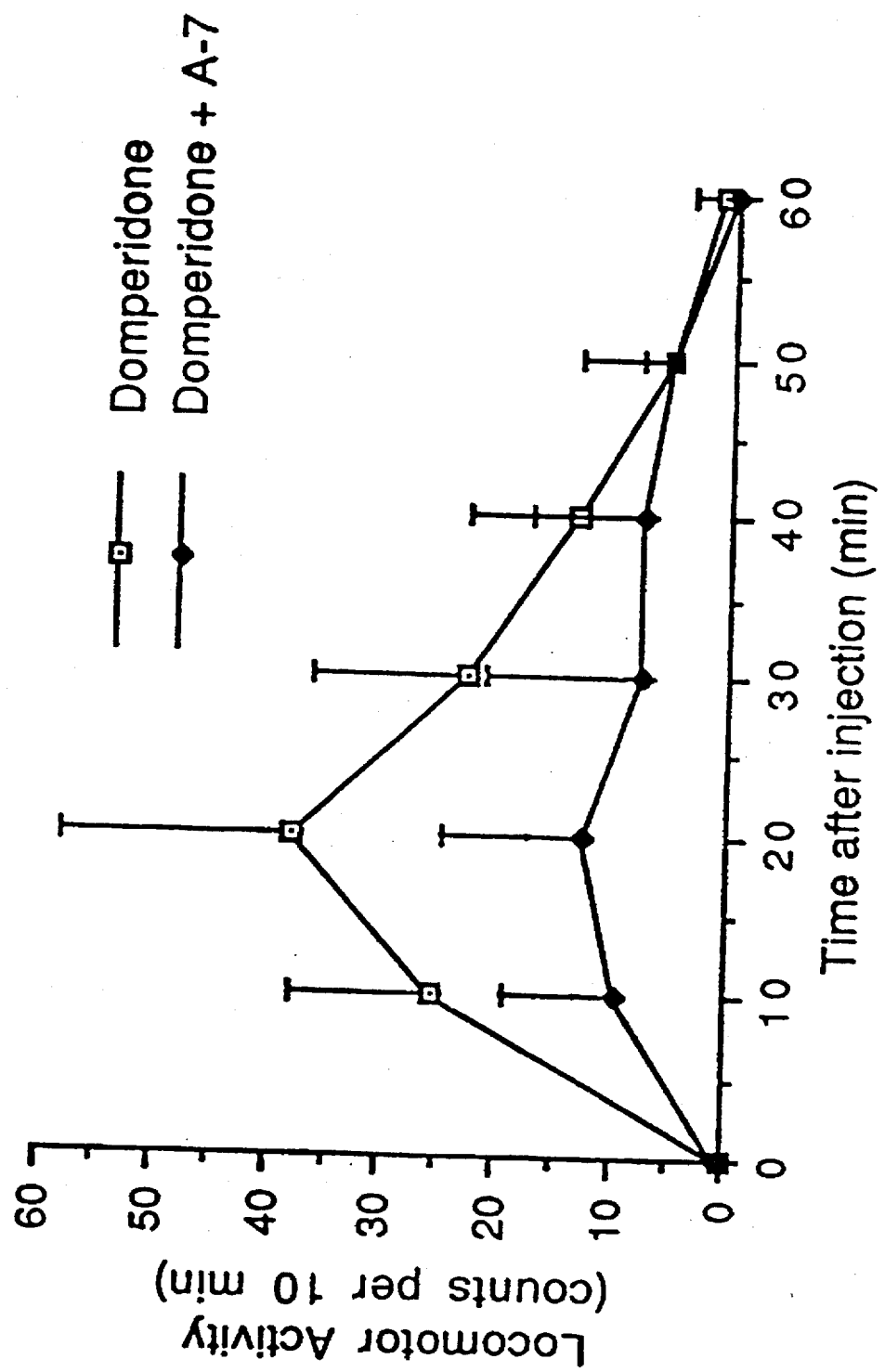
FIG. 8 is a graphic representation of the effects of a dopamine receptor antagonist (domperidone) co-administered with permeabilizer A-7 on apomorphine-induced motor activity of rats.

The results of this experiment with 3 rats in each treatment group are shown in FIG. 8. The combination of permeabilizer A-7 and domperidone antagonized the increase in motor activity associated with apomorphine. Domperidone alone had little, if any, effect on motor activity induced by apomorphine.

EXAMPLE XIV

The Effect of Angiotensin II When Co-administered with Permeabilizer A-7 on the Drinking Behavior of Rats Angiotensin II in supra-physiological concentrations has been shown to induce drinking behavior in water satiated rats. This behavior has been suggested to occur as a result of stimulation of angiotensin II receptors within areas of the brain not associated with the cerebroventricular organs. Studies were performed to evaluate the effect of co-administration of permeabilizer A-7 with an angiotensin II analogue that is capable of causing drinking behavior when administered at a high dose.

Rats were given a coinjection of 10 µg permeabilizer A-7 and either 0.1, 0.3, 3, 10 or 30 µg of β-Asp$^1$-angiotensin II, or the β-Asp$^1$-angiotensin II alone, via a lateral tail vein. The volume of water consumed by each rat over a 1 hour interval was measured.

Figure 9:
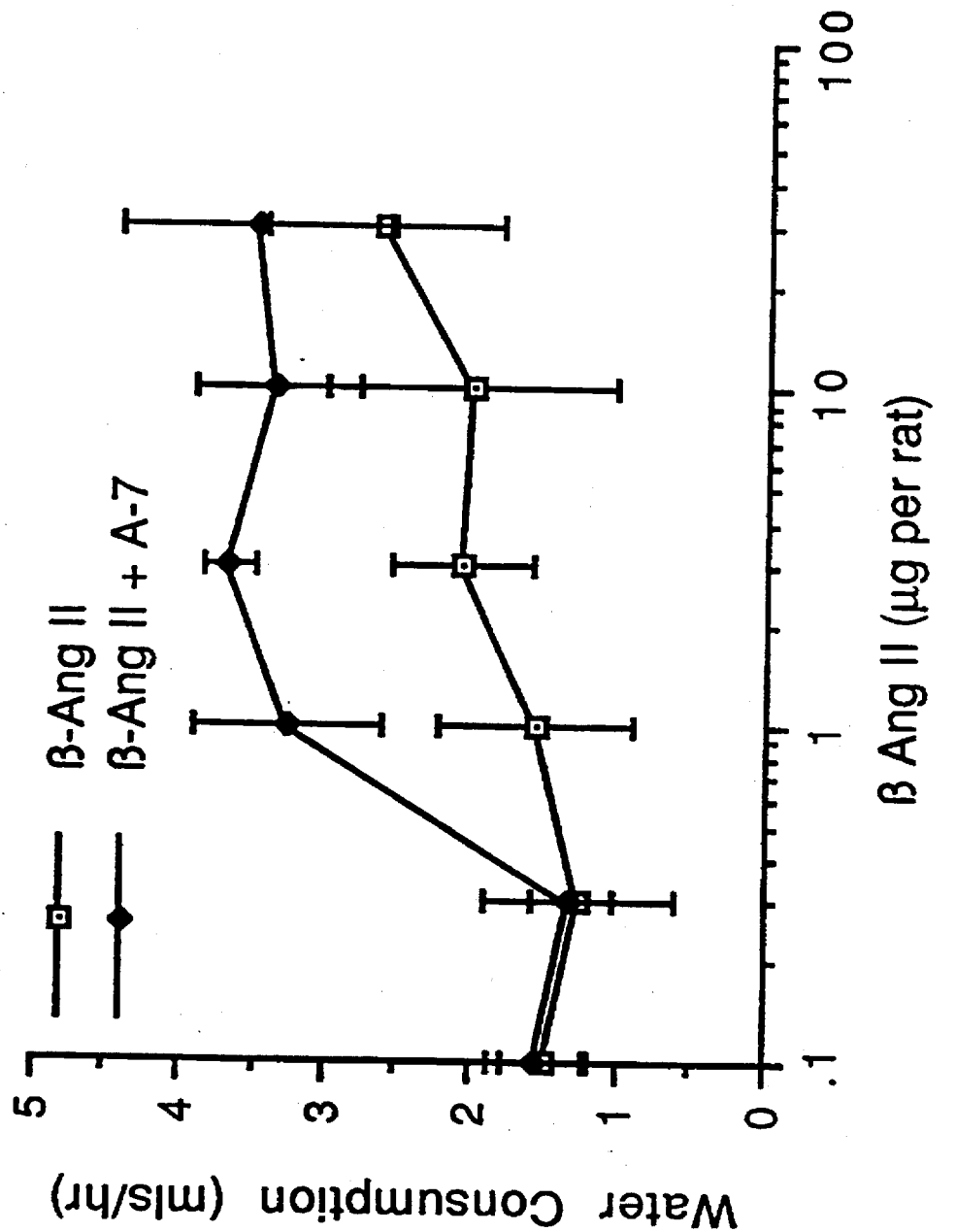
FIG. 9 is a graphic representation of the effects of an angiotensin II analogue co-administered with permeabilizer A-7 on drinking behavior in rats.

The results of this study with 3 rats in each dosage group are shown in FIG. 9. Co-administration of permeabilizer A-7 and the angiotensin II analogue caused the dose response curve to shift to the left, or toward lower doses of analogue, when compared to administration of the analogue alone.

In another study, rats were given either saline, 1 µg of β-Asp$^1$-angiotensin II, 1 µg of β-Asp$^1$-angiotensin II and 10 µg of permeabilizer A-7, 1 µg of β-Asp$^1$-angiotensin II and 8 µg of saralasin, or 1 µg of β-Asp$^1$-angiotensin II plus 10 µg of permeabilizer A-7 plus 8 µg of saralasin via tail vein injection. The saralasin was given because it is a known angiotensin II receptor antagonist. Again, the volume of water consumed by each rat over a 1 hour interval was measured.

Figure 10:
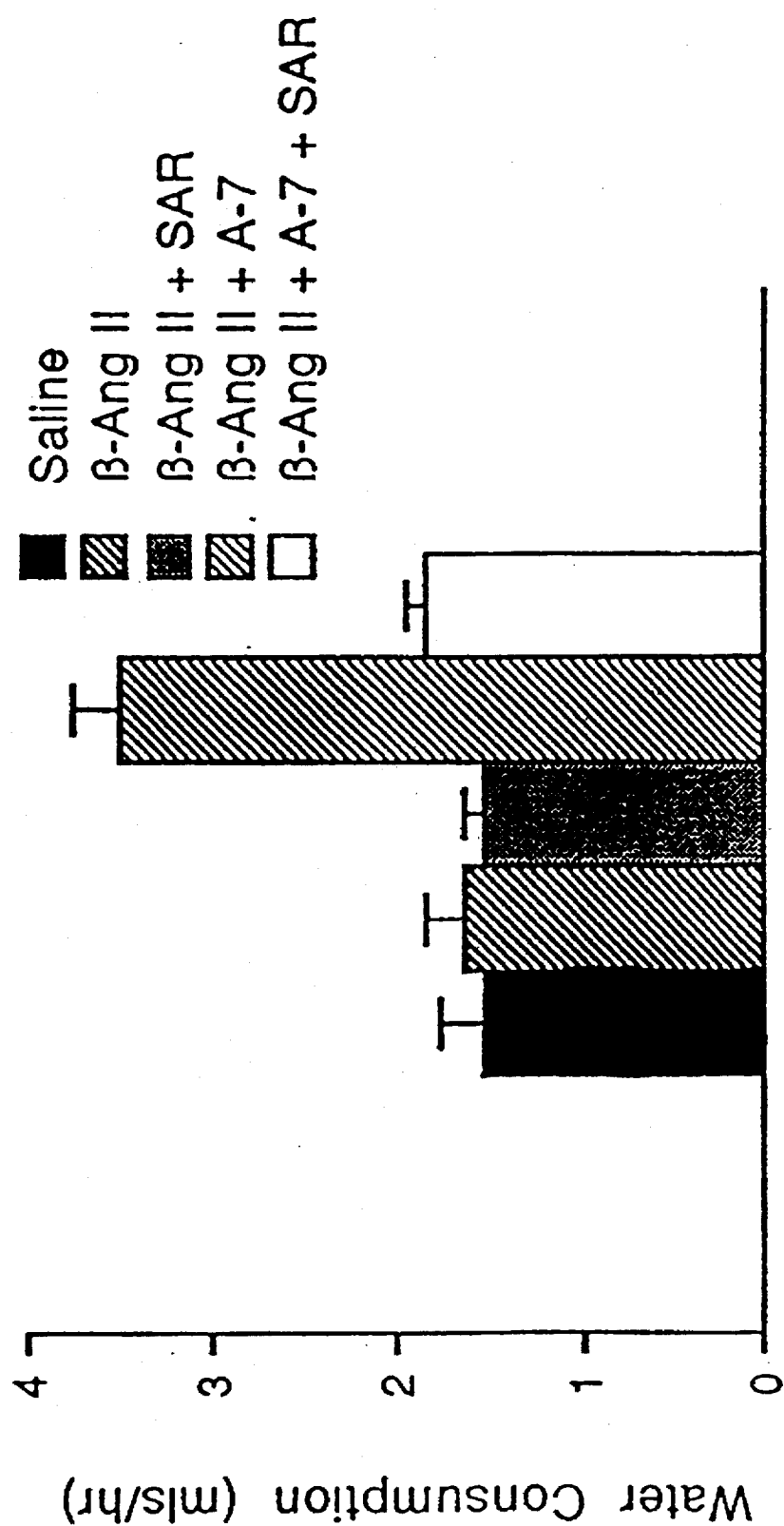
FIG. 10 is a histogram which illustrates the effects of an angiotensin II analogue and inhibitor co-administered with permeabilizer A-7 on drinking behavior in rats.

The results of this study with 3 rats in each group are shown in FIG. 10. The co-administration of permeabilizer

21

A-7 and β-Asp¹-angiotensin II caused a significant increase in water consumption compared to the angiotensin II analogue alone or together with saralasin. When saralasin is co-administered with permeabilizer A-7 and the angiotensin II analogue, the water consumption remained within a normal range which indicates an inhibition of angiotensin II analogue-induced drinking behavior by the addition of the angiotensin II receptor antagonist.

EXAMPLE XV

Figure 11:
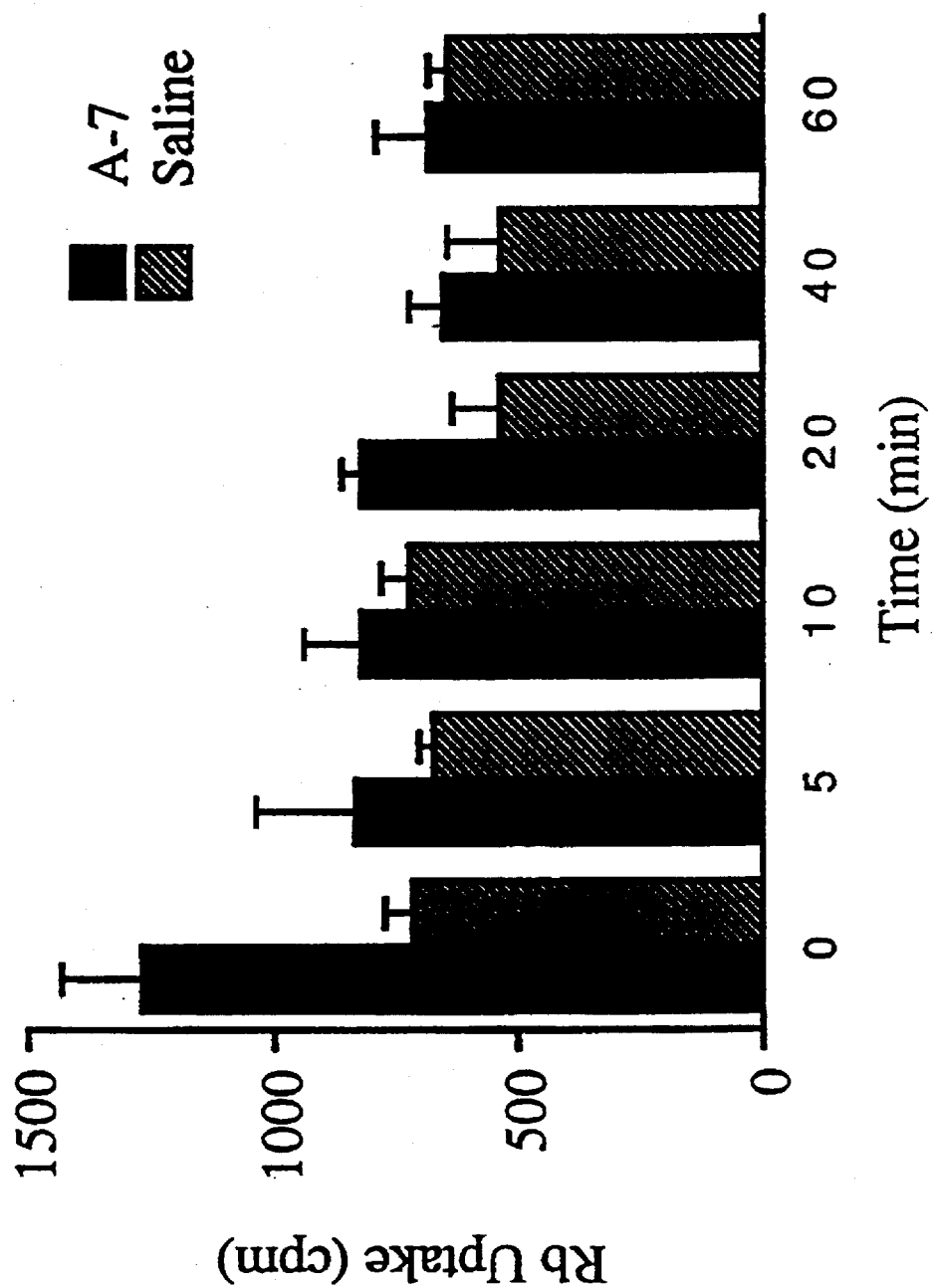
FIG. 11 is a histogram which illustrates the effect of intravenously administered permeabilizer A-7 on the brain uptake of $^{86}$Rb at various times after administration of permeabilizer A-7.

The Effect of Permeabilizer A-7 on the Uptake of $^{86}Rb$ into the Brain of Rats Male Sprague-Dawley rats (200–300 g) were administered 75 μg/kg of permeabilizer A-7 or saline via a lateral tail vein. There were five rats per group. Immediately, 5, 10, 20, 40 or 60 minutes after this injection, $^{86}Rb$ (5000 cpm) was administered into the contralateral tail vein of each rat. Four minutes after receiving $^{86}Rb$, the rats were euthanatized and their brains removed. Each brain was dissected free of pial vessels and radioactivity of the remaining brain tissue was counted in a gamma counter. The brain uptake of $^{86}Rb$ was expressed as counts per minute per brain. These results are shown in FIG. 11 and demonstrate that a greater amount of $^{86}Rb$ is found in the brain of permeabilizer A-7 treated rats when compared to control rats at a very early time following the injection of $^{86}Rb$.

EXAMPLE XVI

The Effects of Permeabilizer A-7 and the 9D-A-7 Diastereomer on Displacement of Bradykinin Binding Endothelial cells employed in this study were isolated from individual rat brain microvessels and cultured. For binding studies, cells at passages 9 to 12 were seeded (at a 1:5 split) onto gelatinized 24-well tissue culture dishes. Binding experiments were conducted on day 7 after seeding. Confluent endothelial cell cultures on 24-well plates were removed from the incubator and each well was washed three times with Dulbecco's Phosphate Buffered Saline (DPBS, 0.2 g/L KCl, 0.2 g/L $KH_2PO_4$, 8 g/L NaCl, 1.15 g/L $Na_2HPO_4$, 0.13 g/L $CaCl_2$ and 0.1 g/L $MgCl_2$—$6H_2O$, pH 7.4), covered with 0.4 mL binding buffer (DPBS and 1% (w/v) bovine serum albumin (BSA), 5 mM 1,0-phenanthroline, and 1% (v/v) ethanol) and then chilled for 15 minutes in a 4° C. cold room. All subsequent manipulations were performed in the cold room, unless otherwise indicated.

Figure 12:
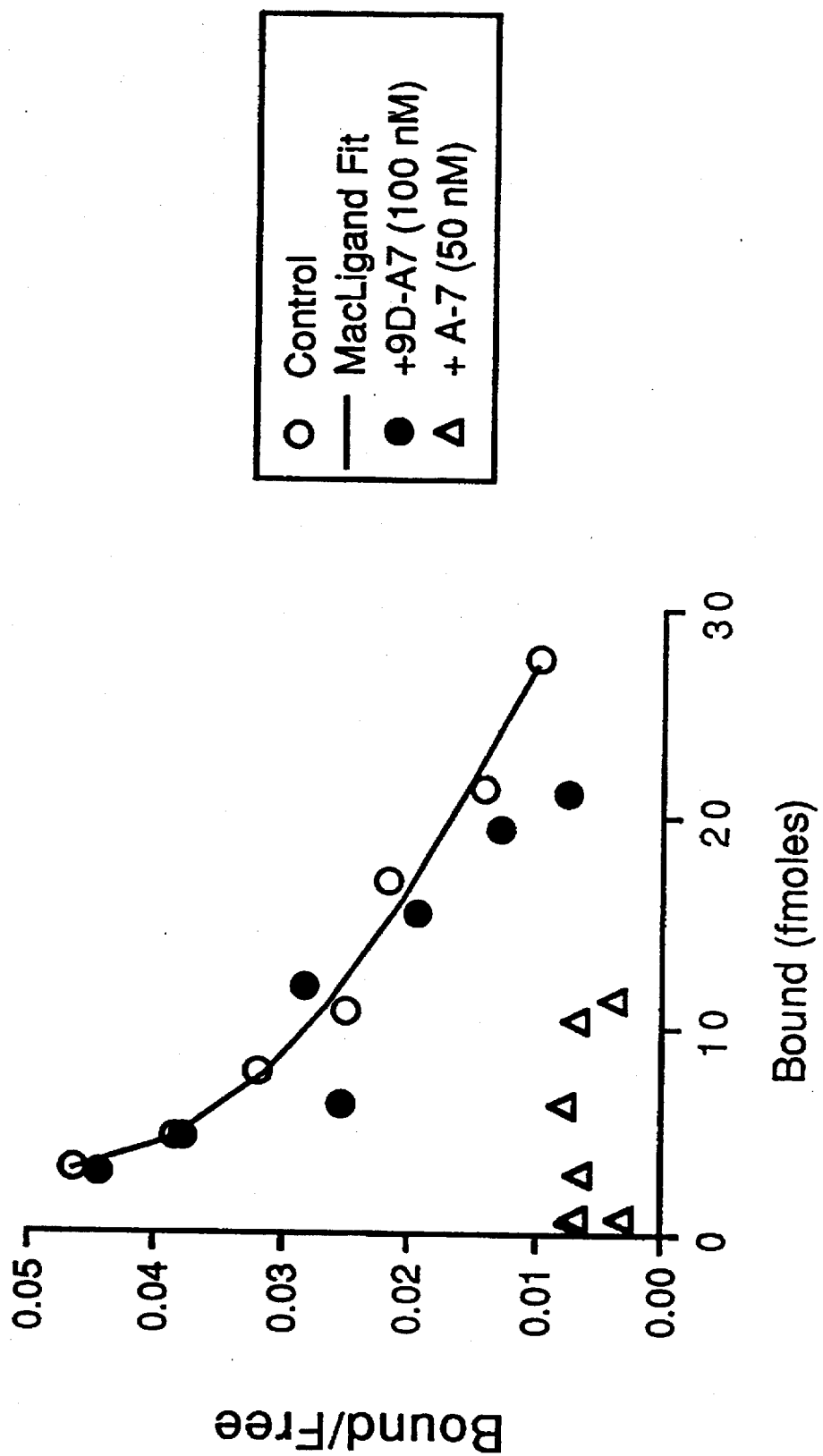
FIG. 12 is a graphic representation of a Scatchard analysis of the specific binding of [$^3$H]-bradykinin in the absence of competing nonradioactive peptide and in the presence of either 50 nM permeabilizer A-7 or 100 nM of the 9D diastereomer of permeabilizer A-7.

To initiate binding incubations, the buffer was removed from cell layers and replaced with 0.4 mL fresh binding buffer at 4° C. containing [$^{3}H$-pro$^{2,3}$]-bradykinin ([$^{3}H$]-bradykinin) and competing non-radioactive peptides at concentrations indicated for the individual experiments. Triplicate wells were used for each experimental condition. For later determination of cell number, where indicated, certain wells were covered with binding buffer without radioligand and incubated in parallel with the other samples. After incubating, the liquid was poured from the wells and the culture dishes were washed rapidly three times in a washing buffer consisting of DPBS with 0.1% BSA. After washing, culture dishes were removed from the cold room for further processing at room temperature.

Where indicated, wells to be assayed for cell number were immediately washed with DPBS without $Ca^{2+}$ and $Mg^{2+}$ and cells were then dissociated from the culture surface with 0.2 mL Trypsin-EDTA (0.25% trypsin, 1 mM EDTA in DPBS without $Ca^{2+}$ and $Mg2+$) per well. The dissociated cells were collected, diluted into 10 mL Isoton diluent, and cell numbers were determined with a Coulter counter. All other samples were collected by solubilizing the cells in each well with two successive aliquots of 0.2 mL 1% (w/v) sodium dodecyl sulfate. The two aliquots were pooled into a single scintillation vial, 10 mL of Hydrofluor scintillation fluid was added and samples were counted for tritium in a scintillation counter. Blank samples, to assess counting background, contained 0.4 mL 1% sodium dodecyl sulfate in 10 mL scintillation fluid. Aliquots of each [$^{3}H$]-bradykinin dilution that was added to the cells were counted along with the other samples. These values were used later to calculate the final concentration of radioligand under each incubation condition. Data were converted to molar amounts of bradykinin using the specific activity of [$^{3}H$]-bradykinin provided by the manufacturer (107 Ci/mmole or 238 dpm/fmole). Error bars represent the standard deviations of replicate samples. Binding data were analyzed by computer using the MacLigand program, version 1.01, available in the public domain. Bradykinin Binding to Rat Brain Endothelial Cells:

The total binding of [$^{3}H$]-bradykinin to rat brain microvascular endothelial cells increased with the concentration of radioligand in the incubation solution. A Scatchard plot of the [$^{3}H$]-bradykinin binding data, corrected for nonspecific binding, appears in FIG. 12 (open circles). As indicated by the curvilinear plot, the data fit well to a model having two affinity classes of [$^{3}H$]-bradykinin binding site. Effect of Permeabilizer A-7 and 9D-A-7 Diastereomer on $^{3}H$-Bradykinin Binding:

The specific binding of [$^{3}H$]-bradykinin to brain endothelial cells in the absence of competing non-radioactive peptide (control, open circles) is compared to the specific binding of [$^{3}H$]-bradykinin observed in the presence of either 50 nM permeabilizer A-7 (open triangles) or 100 nM of the 9D-A-7 diastereomer (closed circles). The solid line represents the curve fitted by MacLigand from data obtained in the absence of competing ligand. As shown in FIG. 12, permeabilizer A-7 displaced [$^{3}H$]-bradykinin from a subset of [$^{3}H$]-bradykinin binding sites. In contrast, 9D-A-7, an inactive isomer, showed no significant effect on radioligand binding.

EXAMPLE XVII

The Effect of Permeabilizer A-7 on the Release of Intracellular Free Calcium in Rat Brain Microvascular Endothelial Cells For intracellular free calcium assays, rat brain endothelial cells at passages 10 to 12 were used. The rat brain endothelial cells were dissociated with 0.02% disodium EDTA in DPBS, seeded (at a 1:5 or 1:10 split) in their growth medium onto fibronectin-coated glass coverslips and allowed to attach and spread in the tissue culture incubator for 2.5 to 3 hr. The coverslips were then removed from the incubator and each was immersed in Leibovitz's (L15) medium. Cells were maintained at 37° C. under room atmosphere until used for experiments.

For experiments, the rat brain microvascular endothelial cells on coverslips were loaded with a calcium-sensitive fluorophore by incubation at 35° C. in Hank's solution (137 mM NaCl, 5.4 mM KCl, 0.44 mM $KH_2PO_4$, 0.42 mM $Na_2HPO_4$, 4.17 mM $NaHCO_3$, 5.55 mM dextrose, 10 mM HEPES, 1 mM $CaCl_2$, 1.4 mM $MgCl_2$ equilibrated with 95% $O_2$–5% $CO_2$, pH 7.4) with 1% albumin, 0.02% Pluronic and a 5 μM concentration of the acetoxymethyl ester form of fura 2 (fura-2 AM) for 20 min. After loading the cells with fura-2 in this manner, the coverslips were washed by dipping them in Hank's solution and then were stored in L15 medium at 35° C. in foil-wrapped dishes until the cells were used for calcium measurements.

Measurements were made on only one cell from a given coverslip and then the coverslip was discarded. Measurements were performed on the stage of an inverted compound microscope equipped for epifluorescence. To make measurements, a coverslip was placed on the microscope stage and covered with 500 μL of Hank's solution. Under the 40×objective of the microscope, a cell was selected for recording and the stage was adjusted so that the light beam passed through the cytoplasm. Fluorescence values were collected with excitation filters of 350±5 nm and 390±6 nm, a 420 nm chromatic beam splitter, and a long path 485 nm filter using a Hamamatsu Model R928 photomultiplier tube and were recorded on a chart recorder. These values were later read from the recorder trace and the ratio of the fluorescence at 350 nm to that at 390 nm, henceforth denoted as "ratio" was calculated. Before applying test peptide, several fluorescence measurements were taken to determine the baseline ratio value reflecting the resting calcium level in the cell. Each test peptide, dissolved in DPBS, was delivered as a 5 μL bolus to the Hank's solution on the coverslip. The concentrations of test peptides reported in the figures are the final concentrations on the coverslip, assuming complete diffusion.

For the permeabilizer A-7 dose-response curve (FIG. 13), data obtained from 5 different cells, with resting ratio values ranging from 0.56 to 0.82, were averaged together. This was accomplished by determining the change in ratio (Δ ratio), or the ratio minus the resting ratio, at the peak of the response. The values were normalized by expressing each Δ ratio measured for an individual cell as the percent of the maximum Δ ratio value observed in that cell. The normalized Δ ratios obtained for each permeabilizer A-7 concentration were averaged and their standard deviations calculated. ANOVA was also performed as described above for the binding studies.

Figure 13:
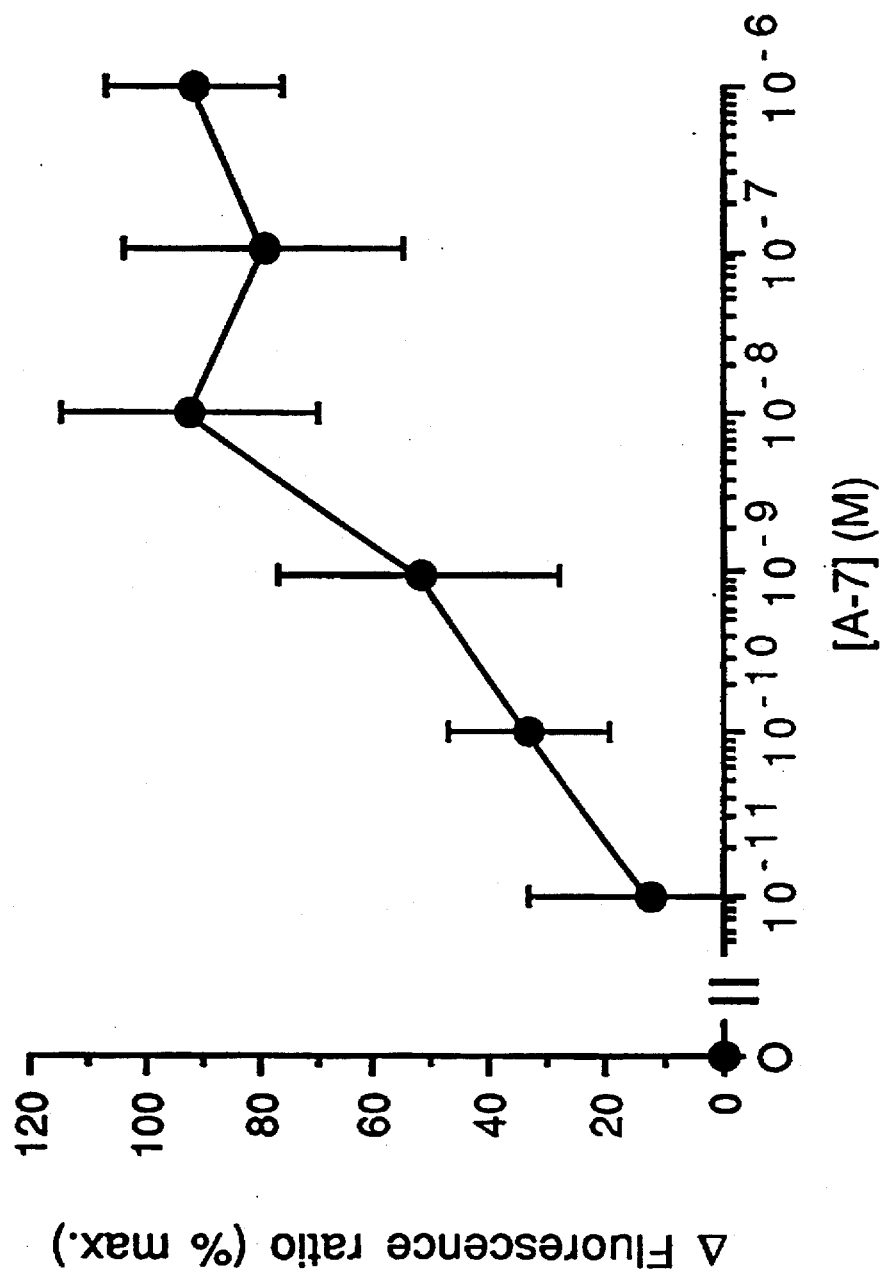
FIG. 13 is a graphic representation of the effects of various concentrations of permeabilizer A-7 on intracellular calcium levels in rat brain endothelial cells.

The data depicted in FIG. 13 indicate that permeabilizer A-7 causes an increase in intracellular free calcium in rat brain microvascular endothelial cells at concentrations as low as $10^{-10}$M. The concentration of permeabilizer A-7 that gives half of the maximum achievable intracellular calcium release by this technique ($ED_{50}$) is approximately $10^{-9}$M. In addition, the permeabilizer A-7 induced intracellular calcium release appears to be saturated at permeabilizer A-7 concentrations above $10^{-8}$M.

EXAMPLE XVIII

Figure 14:
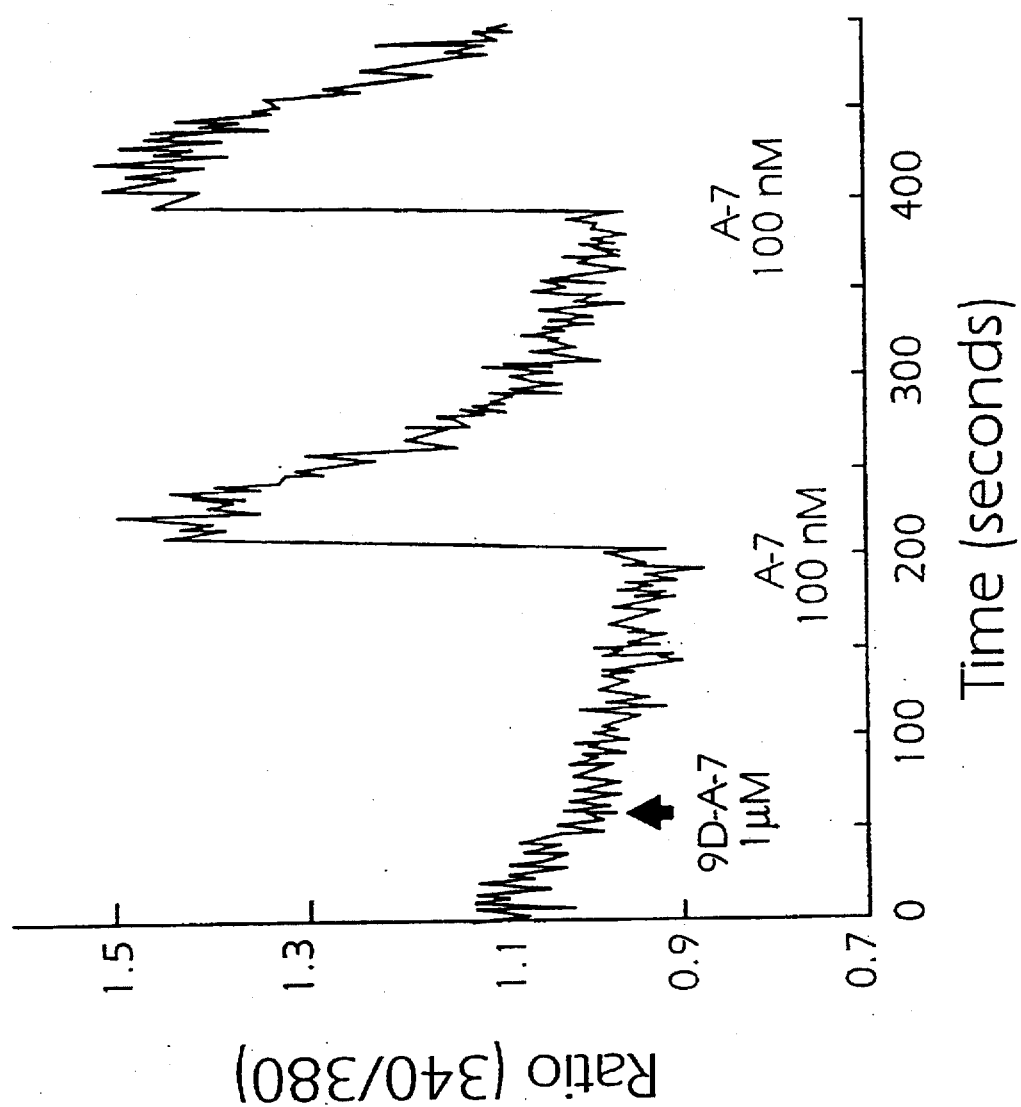
FIG. 14 is a tracing of changes in fluorescence ratios from a rat brain endothelial cell exposed to permeabilizer A-7 and the 9D diastereomer of permeabilizer A-7.

Effects of Permeabilizer A-7 and 9D-A-7 on Intracellular Free Calcium in Rat Brain Endothelial Cells The binding studies of Example XVI suggest that permeabilizer A-7 binds to at least one class of bradykinin receptor on brain endothelial cells. To address whether permeabilizer A-7 acts as a bradykinin receptor agonist in these cultures, effects of the peptide on intracellular calcium mobilization, a signal transduction event that is known to occur in bradykinin-stimulated endothelial cells, was investigated using quantitative fluorescence microscopy as described in the previous Example. FIG. 14 shows the kinetics of fura-2 fluorescence ratio changes in a single rat brain endothelial cell stimulated with permeabilizer A-7 or 9D-A-7. This cell was first treated with 1 μM 9D-A-7 and exhibited no change in intracellular free calcium. However, two successive stimulations with 100 nM of permeabilizer A-7 each caused a rapid increase in intracellular free calcium that decayed to a sustained level, above baseline, over a period of about 100 sec.

EXAMPLE XIX

Effect of Permeabilizer A-7 in the Treatment of Intracisternal Cryptococcal Infections with Amphotericin B Amphotericin B (AmB), a polyene macrolide, is currently being used for the treatment of fungal meningitis in humans. The treatment of experimentally-induced cryptococcal meningitis in rabbits parallels many of the features of this infection in humans. However, the penetration of AmB into cerebrospinal fluid (CSF) is quite low, and the CSF concentration of AmB in vivo does not correlate well with its activity against the growth of *Cryptococcus neoformans in vitro*. In addition, the administration of AmB is associated with nephrotoxicity and other serious side effects. Therapies that could increase AmB CSF concentrations could be beneficial in the treatment of this fungal infection. Therefore, a study was performed to evaluate whether co-administration of permeabilizer A-7 and AmB would be more effective than AmB alone in the treatment of experimentally induced cryptococcal meningitis in rabbits.

Four day old cultures of *C. neoformans* containing 100 μg of chloramphenicol per mL were absorbed on cotton swabs, suspended in 15 mM phosphate-buffered saline, and adjusted to approximately $5 \times 10^7$ colony forming units (CFU)/mL. New Zealand White rabbits (2–3 kg) were immunosuppressed with 2.5 mg cortisone acetate administered intramuscularly (i.m.) beginning one day prior to inoculation with *C. neoformans* (Day 0), and once daily thereafter until study termination. On Day 1 rabbits were sedated with ketamine (100–150 mg) and xylazine (15–25 mg) i.m., and intracisternally inoculated with 0.3 mL of *C. neoformans* suspension. On Day 4 CSF was collected and plated on agar plates containing chloramphenicol to establish a baseline level for *C. neoformans* counts (CFU/mL), and drug treatment was then initiated. CSF samples were also withdrawn for *C. neoformans* counts on Days 7, 11 and 14. The duration of drug treatment was 10 days.

Rabbits were administered one of the following intravenous treatment regimens: 1) saline-control; 2) 1 mg AmB/kg/day; 3) 10 ng permeabilizer A-7/kg/day +1 mg AmB/kg/day; 4) 100 ng permeabilizer A-7/kg/day +1 mg AmB/kg/day. Each group size generally consisted of three to five animals. All treatments were administered via an ear vein, and permeabilizer A-7 was always administered immediately prior to AmB. CSF samples were always withdrawn prior to drug therapy on treatment days.

Figure 15:
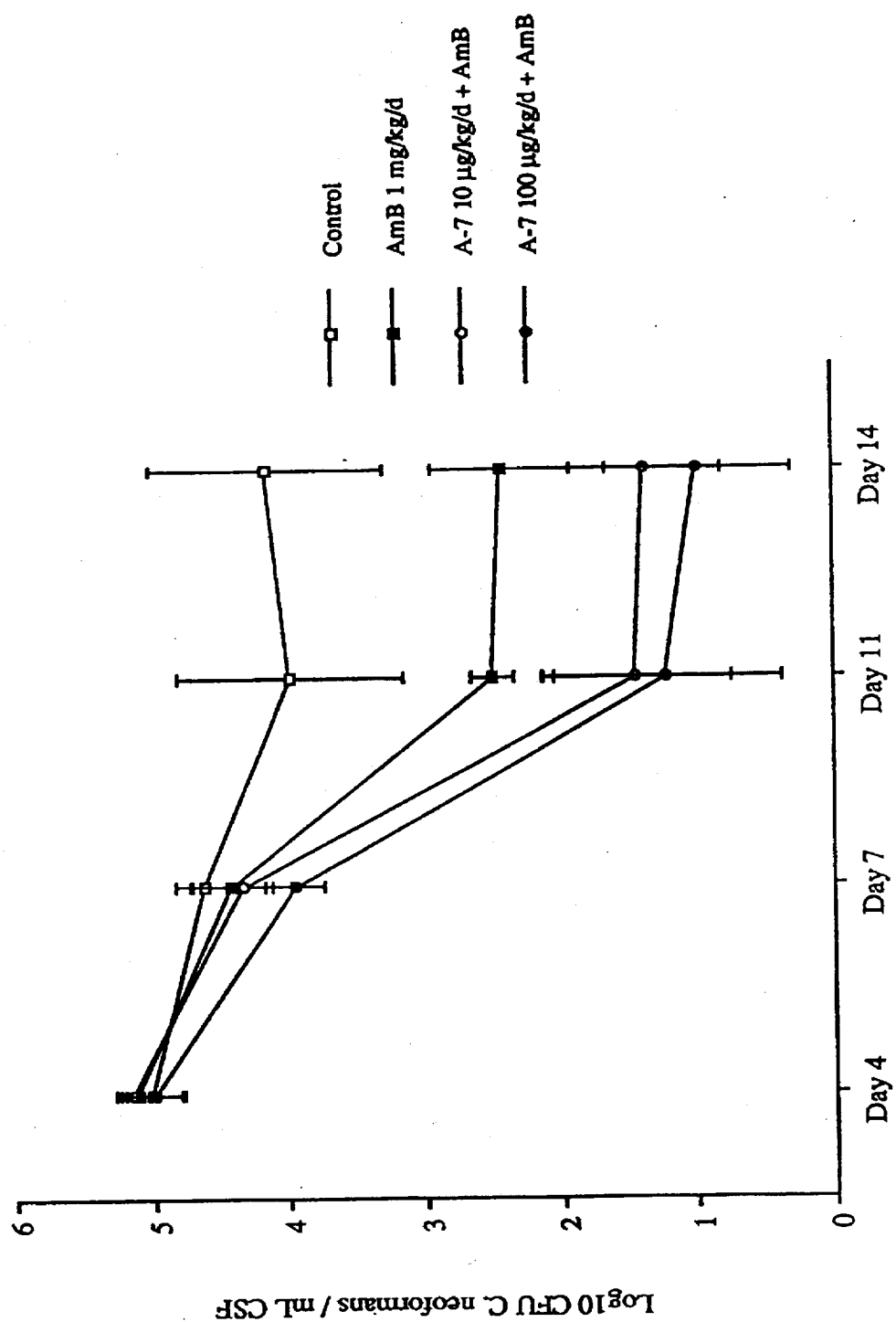
FIG. 15 is a graphic representation of the effects of permeabilizer A-7 on the effectiveness of amphotericin B against experimentally-induced cryptococcal meningitis.

The effects of AmB and permeabilizer A-7 on CSF *C. neoformans* counts in rabbits with experimentally-induced cryptococcal meningitis are presented in FIG. 15. control *C. neoformans* counts remained relatively constant for the duration of the study. Daily treatment with 1 mg AmB/kg significantly lowered *C. neoformans* counts on Days 11 and 14 when compared to controls. The combination of 100 ng permeabilizer A-7 /kg/day and 1 mg AmB/kg/day lowered *C. neoformans* counts on Day 7 to slightly below those of any other treatment group. The simultaneous administration of 1 mg AmB/kg/day and permeabilizer A-7 (at both 10 and 100 ng permeabilizer A-7/kg/day) further attenuated colony counts compared to either control or AmB treatment on Days 11 and 14. In fact, on Day 11, sterile CSF cultures were observed in 40% of animals administered the combination of 10 ng permeabilizer A-7/kg/day+1 mg AmB/kg/day, and in 60% of rabbits given 100 ng permeabilizer A-7/kg/day+1 mg AmB/kg/day (data not shown). No sterile CSF cultures were noted in any other treatment group.

These findings suggest that the permeabilizer A-7 increases the efficacy of AmB in treating experimentally-induced cryptococcal meningitis in rabbits, evidenced by lower colony counts after seven (Day 11) and ten days (Day 14) of therapy. Furthermore, slightly lower *C. neoformans* counts in animals treated daily with 100 ng permeabilizer A-7/kg and 1 mg AmB/kg for three days (Day 7) suggest that this combination may more rapidly inhibit *C. neoformans* growth compared to the standard AmB therapy.

We claim:

1. A peptide having the amino acid sequence of R-arginine-proline-hydroxyproline-glycine-thienylalanine-serine-proline-(4-Me-tyrosine)ψ(CH$_2$NH)arginine-OH (SEQ ID NO.:1) or a conformational analogue thereof which is said peptide with at least one of the following modifications:

a) the arginine closest to R is replaced by an amino acid analogue containing a guanidino side chain;

b) the proline closest to R is replaced by hydroxyproline, dehydroproline or N-methylalanine;

c) the hydroxyproline is replaced by proline, dehydroproline, alanine or N-methylalanine;

d) the thienylalanine is replaced by another aromatic amino acid or a hydrophobic aliphatic amino acid;

e) the serine is replaced by glycine or alanine;

f) the proline closest to the C-terminal is replaced by hydroxyproline, dehydroproline or N-methylalanine; and g) the C-terminal arginine is replaced by an amino acid analogue containing a guanidino side chain;

wherein R is selected from the group consisting of acetyl, arginine, acetyl arginine, propyl arginine, benzyl arginine, arginine—arginine, methionine-arginine, lysine, lysine—lysine and methionine-lysine.

2. The peptide of claim 1 wherein said modification is chosen from:

a) β-cycloarginine, homoarginine, γ-hydroxyarginine, canavanine, N$^ω$-amidinocitrulline, 2-amino-4-guanidobutanoic acid for the arginine closest to R or the C-terminal arginine;

b) hydroxyproline or dehydroproline for the proline closest to R or the proline closest to the C-terminal;

c) proline or dehydroproline for the hydroxyproline;

d) dehydrophenylalanine, phenylalanine or another aromatic amino acid for the thienylalanine; and e) glycine for serine.

3. The peptide of claim 1 wherein all optically active amino acids are of the L-configuration.

4. The peptide of claim 1 wherein the 4-Me-tyrosine is of the D-configuration.

5. A pharmaceutical composition for administration to an animal to increase the permeability of the blood-brain barrier to a molecule, comprising:

a) an effective amount of a peptide having the amino acid sequence of R-arginine-proline-hydroxyproline-glycine-thienylalanine-serine-proline-(4-Me-tyrosine)ψ(CH$_2$NH)arginine-OH (SEQ ID No.:1) or a conformational analogue thereof which is said peptide with at least one of the following modifications:

i) the arginine closest to R is replaced by an amino acid analogue containing a guanidino side chain;

ii) the proline closest to R is replaced by hydroxyproline, dehydroproline or N-methylalanine;

iii) the hydroxyproline is replaced by proline, dehydroproline, alanine or N-methylalanine;

iv) the thienylalanine is replaced by another aromatic amino acid or a hydrophobic aliphatic amino acid;

v) the serine is replaced by glycine or alanine;

vi) the proline closest to the C-terminal is replaced by hydroxyproline, dehydroproline or N-methylalanine; and vii) the C-terminal arginine is replaced by an amino acid analogue containing a guanidino side chain;

wherein R is selected from the group consisting of acetyl, arginine, acetyl arginine, propyl arginine, benzyl arginine, arginine—arginine, methionine-arginine, lysine, lysine—lysine and methionine-lysine; and b) a pharmaceutically acceptable carrier.

6. A method for increasing the permeability of the blood-brain barrier of a host in need of treatment with a molecule passing through the blood-brain barrier comprising administering intravenously to said host an effective amount of a bradykinin agonist of blood-brain barrier permeability; said agonist being effective for increasing blood-brain barrier permeability to said molecule.

7. A method for increasing the permeability of the blood-brain barrier of a host in need of treatment with a molecule passing through the blood-brain barrier comprising co-administering an effective amount of a bradykinin agonist of blood-brain barrier permeability intravenously to said host and said molecule either intravenously or intra-arterially to said host; said agonist being effective for increasing blood-brain barrier permeability to said molecule.

8. A method for increasing the permeability of the blood-brain barrier of a host to carboplatin present in the bloodstream of the host comprising the intravascular administration of an effective amount of a blood-brain barrier permeabilizer comprising a peptide with the amino acid sequence of [H]R-arginine-proline-hydroxyproline-glycine-thienylalanine-serine-proline-(4-Me-tyrosine)ψ(CH$_2$NH) arginine-OH (SEQ ID NO: 1) or a conformational analogue thereof which is said peptide with at least one of the following modifications:

a) the arginine closest to R is replaced by an amino acid analogue containing a guanidino side chain;

b) the proline closest to R is replaced by hydroxyproline, dehydroproline or N-methylalanine;

c) the hydroxyproline is replaced by prolinee dehydroproline,ko alanine or N-methylalanine;

d) the thienylalanine is replaced by another aromatic amino acid or a hydrophobic aliphatic amino acid;

e) the serine is replaced by glycine or alanine;

f) the proline closest to the C-terminal is replaced by hydroxyproline, dehydroproline or N-methylalanine; and g) the C-terminal arginine is replaced by an amino acid analogue containing a guanidino side chain;

wherein R is selected from the group consisting of H, acetyl, arginine, acetyl arginine, propyl arginine, benzyl arginine, arginine—arginine, methionine-arginine, lysine, lysine—lysine and methionine-lysine.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
       ( A ) LENGTH: 9 amino acids
       ( B ) TYPE: amino acid
       ( D ) TOPOLOGY: linear ( i i ) MOLECULE TYPE: peptide ( i i i ) HYPOTHETICAL: NO ( v i ) ORIGINAL SOURCE:
       ( C ) INDIVIDUAL ISOLATE: Synthesized ( i x ) FEATURE:
       ( A ) NAME/KEY: Modified-site
       ( B ) LOCATION: 3
       ( D ) OTHER INFORMATION: /label=other
             / note= "hydroxyproline"

( i x ) FEATURE:
       ( A ) NAME/KEY: Modified-site
       ( B ) LOCATION: 5
       ( D ) OTHER INFORMATION: /label=other
             / note= "thienylalanine"

( i x ) FEATURE:
       ( A ) NAME/KEY: Modified-site
       ( B ) LOCATION: 8
       ( D ) OTHER INFORMATION: /label=other
             / note= "substituent is a 4-methyl group"

( i x ) FEATURE:
       ( A ) NAME/KEY: Modified-site
       ( B ) LOCATION: 8..9
       ( D ) OTHER INFORMATION: /label=other
             / note= "reduced peptide bond"

( x i ) SEQUENCE DESCRIPTION: SEQ ID NO:1:

Arg Pro Xaa Gly Xaa Ser Pro Tyr Arg
   1               5

( 2 ) INFORMATION FOR SEQ ID NO:2:

( i ) SEQUENCE CHARACTERISTICS:
       ( A ) LENGTH: 9 amino acids
       ( B ) TYPE: amino acid
       ( D ) TOPOLOGY: linear ( i i ) MOLECULE TYPE: peptide ( i i i ) HYPOTHETICAL: NO ( x ) PUBLICATION INFORMATION:
       ( A ) AUTHORS: Marceau,
             et al.,
       ( B ) TITLE: Pharmacology of Kinins: Their Relevance to
             Tissue Injury and Inflammation
       ( C ) JOURNAL: General Pharmacology
       ( D ) VOLUME: 14
       ( E ) ISSUE: 2
       ( F ) PAGES: 209-229
       ( G ) DATE: 1983

( x i ) SEQUENCE DESCRIPTION: SEQ ID NO:2:

Arg Pro Pro Gly Phe Ser Pro Phe Arg
   1               5